US009988341B2

(12) United States Patent
Tse-Dinh et al.

(10) Patent No.: US 9,988,341 B2
(45) Date of Patent: Jun. 5, 2018

(54) BACTERIAL TOPOISOMERASE INHIBITORS AND USE THEREOF

(71) Applicants: Yuk-Ching Tse-Dinh, Coral Gables, FL (US); Marcello Angelo Giulianotti, Vero Beach, FL (US); Richard Allen Houghten, Port St. Lucie, FL (US)

(72) Inventors: Yuk-Ching Tse-Dinh, Coral Gables, FL (US); Marcello Angelo Giulianotti, Vero Beach, FL (US); Richard Allen Houghten, Port St. Lucie, FL (US)

(73) Assignees: THE FLORIDA INTERNATIONAL UNIVERSITY BOARD OF TRUSTEES, Miami, FL (US); TORREY PINES INSTITUTE FOR MOLECULAR STUDIES, Port St. Lucie, FL (US)

( * ) Notice: Subject to any disclaimer, the term of this patent is extended or adjusted under 35 U.S.C. 154(b) by 0 days. days.

(21) Appl. No.: 15/491,679

(22) Filed: Apr. 19, 2017

(65) Prior Publication Data

US 2017/0298004 A1    Oct. 19, 2017

Related U.S. Application Data

(60) Provisional application No. 62/324,772, filed on Apr. 19, 2016.

(51) Int. Cl.
*C07C 211/30* (2006.01)
*A61K 31/192* (2006.01)

(52) U.S. Cl.
CPC .................. *C07C 211/30* (2013.01)

(58) Field of Classification Search
CPC combination set(s) only.
See application file for complete search history.

(56) References Cited

U.S. PATENT DOCUMENTS 6,768,024 B1 * 7/2004 Watson-Straughan ............ C07C 211/27
544/107

FOREIGN PATENT DOCUMENTS

WO    WO-2017079609 A1 *  5/2017    ........... C07C 311/18

OTHER PUBLICATIONS

Chemical Abstract Service, STN Registry Database [online], Registry No. 1222768-24-2 [Entered STN May 13, 2010]. (Year: 2010).*
Chemical Abstract Service STN Registry Database [online], Registry No. 754164-09-5 [Entered STN Sep. 29, 2004]. (Year: 2004).*
Chemical Abstract Service STN Registry Database [online], Registry No. 742049-89-4 [Entered STN Sep. 10, 2004]. (Year: 2004).*
Chemical Abstract Service STN Registry Database [online], Registry No. 1348782-90-0 [Entered STN Dec. 5, 2011]. (Year: 2011).*
Chemical Abstract Service STN Registry Database [online], Registry No. 775551-73-0 [Entered STN Nov. 7, 2004]. (Year: 2004).*
Acharya, A.N. et al., "Determination of Isokinetic Ratios Necessary for Equimolar Incorporation of Carboxylic Acids in the Solid-Phase Synthesis of Mixture-Based Combinatorial Libraries." *Biopolymers*, May 2002, 65:32-39, doi: 10.1002/bip.10206.
Ahmed, W. et al., "Conditional Silencing of Topoisomerase I Gene of *Mycobacterium tuberculosis* Validates Its Essentiality for Cell Survival." *FEMS Microbiol. Lett.*, Apr. 2014, 353:116-123, doi: 10.1111/1574-6968.12412.
Aldred, K.J., "Mechanism of Quinolone Action and Resistance in Bacterial and Human Type II Topoisomerases." *Biochemistry*, May 2014, pp. 1-158, doi: 10.1021/bi5000564.
Andreu, N. et al., "Optimisation of Bioluminescent Reporters for Use with Mycobacteria." *PLoS ONE*, May 2010, 5(5):1-16, doi: 10.1371/journal.pone.0010777.
Bansal, S. et al., "3,4-Dimethoxyphenyl Bis-Benzimidazole, a Novel DNA Topoisomerase Inhibitor that Preferentially Targets *Escherichia coli* Topoisomerase I." *J. Antimicrob. Chemother.*, Sep. 2012, 67:2882-2891, doi: 10.1093/jac/dks322.
Chen, S.H. et al., "New Mechanistic and Functional Insights into DNA Topoisomerases." *Annu. Rev. Biochem.*, Mar. 2013, 82:139-170, doi: 10.1146/annurev-biochem-061809-100002.
Cheng, B. et al., "Compounds with Antibacterial Activity that Enhance DNA Cleavage by Bacterial DNA Topoisomerase I." *Journal of Antimicrobial Chemotherapy*, Feb. 2007, 59:640-645, doi: 10.1093/jac/dkl556.
Dinardo, S. et al., "*Escherichia Coll* DNA Topoisomerase I Mutants Have Compensatory Mutations in DNA Gyrase Genes." *Cell*, Nov. 1982, 31:43-51, doi: 0092-8674(82)90403-2.
Drlica, K., "Control of Bacterial DNA Supercoiling." *Molecular Microbiology*, Feb. 1992, 6:425-433.
Engström, A., "Fighting an Old Disease with Modern Tools: Characteristics and Molecular Detection Methods of Drug-Resistant *Mycobacterium tuberculosis.*" *Infectious Diseases*, Jul. 2015, 48(1):Abstract, doi: 10.3109/23744235.2015.1061205.
Friedman, N.D. et al., "The Negative Impact of Antibiotic Resistance." *Clinical Microbiology and Infection*, May 2016, 22(5):Abstract, doi: 10.1016/j.cmi.2015.12.002.
García, M.T. et al., "New Alkaloid Antibiotics That Target the DNA Topoisomerase I of *Streptococcus pneumoniae.*" *The Journal of Biological Chemistry*, Feb. 2011, 286(8):6402-6413, doi: 10.1074/jbc.M110.148148.
Godbole, A.A. etal., "Inhibition of Mycobacterium Tuberculosis Topoisomerase I by M-AMSA, a Eukaryotic Type II Topoisomerase Poison." *Biochemical and Biophysical Research Communications*, Mar. 2014, 446: 916-920, doi: 10.1016/j.bbrc.2014.03.029.
Houghten, R.A., "General Method for the Rapid Solid-Phase Synthesis of Large Numbers of Peptides: Specificity of Antigen-Antibody Interaction at the Level of Individual Amino Acids." *Proc. Natl. Acad. Sci. USA*, Aug. 1985, 82:5131-5135.

(Continued)

*Primary Examiner* — Amanda L Aguirre
(74) *Attorney, Agent, or Firm* — Saliwanchik, Lloyd & Eisenschenk

(57) ABSTRACT

The present invention provides novel compounds as bacterial topoisomerase inhibitors with antibacterial activity. The present invention also provides pharmaceutical compositions comprising at least one of the compounds and methods of using the compounds and pharmaceutical compositions as antibacterial agents for treating infectious diseases.

11 Claims, 6 Drawing Sheets

(56) References Cited

OTHER PUBLICATIONS

Houghten, R.A. et al., "Mixture-Based Synthetic Combinatorial Libraries." *Journal of Medicinal Chemistry*, Sep. 1999, 42(19):3743-3778.

Houghten, R.A. et al., "Strategies for the Use of Mixture-Based Synthetic Combinatorial Libraries: Scaffold Ranking, Direct Testing In Vivo, and Enhanced Deconvolution by Computational Methods." *J. Comb. Chem.*, Dec. 2008, 10(1):3-19, doi: 10.1021/cc7001205.

Manku, S. et al., "A Mild and General Solid-Phase Method for the Synthesis of Chiral Polyamines. Solution Studies on the Cleavage of Borane-Amine Intermediates from the Reduction of Secondary Amides." *J. Org. Chem.*, Feb. 2001, 66:874-885, doi: 10.1021/jo005647g.

Massé, E., Drolet, M., "Relaxation of Transcription-Induced Negative Supercoiling is an Essential Function of *Escherichia coli* DNA Topoisomerase I." *The Journal of Biological Chemistry*, Jun. 1999, 274(23):16654-16658, doi: 10.1074/jbc.274.23.16654.

Matteelli, A. et al., "Extensively Drug-Resistant Tuberculosis: Epidemiology and Management." *Clinical Epidemiology*, Apr. 2014, 6:111-118, doi: 10.2147/CLEP.S35839.

Narula, G., Tse-Dinh, Y.-C., "Residues of *E. coli* Topoisomerase I Conserved for Interaction With a Specific Cytosine Base to Facilitate DNA Cleavage." *Nucleic Acids Research*, Jul. 2012, 40(18):9233-9243, doi: 10.1093/nar/gks688.

Nefzi, A. et al., "Combinatorial Chemistry: Libraries from Libraries, the Art of the Diversity-Oriented Transformation of Resin-Bound Peptides and Chiral Polyamides to Low Molecular Weight Acyclic and Heterocyclic Compounds." *J. Org. Chem.*, May 2004, 69:3603-3609, doi: 10.1021/jo040114j.

Nefzi, A. et al., "Parallel Solid Phase Synthesis of Tetrasubstituted Diethylenetriamines via Selective Amide Alkylation and Exhaustive Reduction of N-Acylated Dipeptides." *Tetrahedron*, Jan. 1999, 55(2):335-344, doi: 10.1016/S0040-4020(98)01043-6.

Nefzi, A. et al., "Solid-Phase Synthesis of Bis-Heterocyclic Compounds from Resin-Bound Orthogonally Protected Lysine." *J. Comb. Chem.*, Jan.-Feb. 2001, 3(1):68-70, doi: 10.1021/cc000061t.

Nimesh, H. et al., "Synthesis and Biological Evaluation of Novel Bisbenzimidazoles as *Escherichia coli* Topoisomerase IA Inhibitors and Potential Antibacterial Agents." *J. Med. Chem.*, May 2014, 57:5238-5257, doi: 10.1021/jm5003028.

Ostresh, J.M. et al., "Peptide Libraries—Determination of Relative Reaction-Rates of Protected Amino-Acids in Competitive Couplings." *Biopolymers*, Dec. 1994, 34(12):Abstract.

Ostresh, J.M. et al., "Solid-Phase Synthesis of Trisubstituted Bicyclic Guanidines via Cyclization of Reduced N-Acylated Dipeptides." *J. Org. Chem.*, Jun. 1998, 63:8622-8623, doi: 10.1021/jo9810617.

Pinilla, C. et al., "Rapid Identification of High Affinity Peptide Ligands Using Positional Scanning Synthetic Peptide Combinatorial Libraries." *Biotechniques*, Dec. 1992, 13(6):Abstract.

Pruss, G.J. et al., "*Escherichia coli* DNA Topisomerase I Mutants: Increased Supercoiling is Corrected by Mutations Near Gyrase Genes." *Cell*, Nov. 1982, 31:35-42.

Ravishankar, S. et al., "Genetic and Chemical Validation Identifies *Mycobacterium tuberculosis* Topoisomerase I as an Attractive Anti-Tubercular Target." *Tuberculosis*, May 2015, 95:589-598, doi: 10.1016/j.tube.2015.05.004.

Reilley, K.J. et al., "Identification of Two Novel, Potent, Low-Liability Antinociceptive Compounds from the Direct In Vivo Screening of a Large Mixture-Based Combinatorial Library." *The AAPS Journal*, Sep. 2010, 12(3):318-329, doi: 10.1208/s12248-010-9191-3.

Santos, R.G. et al., "The Mathematics of a Successful Deconvolution: A Quantitative Assessment of Mixture-Based Combinatorial Libraries Screened Against Two Formylpeptide Receptors." *Molecules*, May 2013, 18(6):6408-6424, doi: 10.3390/molecules18066408.

Schoeffler, A.J., Berger, J.M., "DNA topoisomerases : Harnessing and Constraining Energy to Govern chromosometopology." *Quarterly Reviews of Biophysics*, Feb. 2008, 41(1):41-101, doi: 10.1017/S003358350800468X.

Suerbaum, S. et al., "Topoisomerase I of *Helicobacter pylori*: Juxtaposition With a Flagellin Gene (*flaB*) and Functional Requirement of a Fourth Zinc Finger Motif." *Gene*, Jan. 1998, 210:151-161.

Tan, K. et al., "Structural Basis for Suppression of Hypernegative DNA Supercoiling by *E. coli* Topoisomerase I." *Nucleic Acids Research*, Oct. 2015, 43(22):11031-11046, doi: 10.1093/nar/gkv1073.

Tang, S.C., Shapiro, T.A., "Newly Identified Antibacterial Compounds are Topoisomerase Poisons in African Trypanosomes." *Antimicrobial Agents and Chemotherapy*, Feb. 2010, 54(2):620-626, doi: 10.1128/AAC.01025-09.

Tomašić, T., Mašič, L.P., "Prospects for Developing New Antibacterials Targeting Bacterial Type IIA Topoisomerases." *Current Topics in Medicinal Chemistry*, 2014, 14:130-151.

Tse-Dinh, Y.-C., "Bacterial Topoisomerase I as a Target for Discovery of Antibacterial Compounds." *Nucleic Acids Research*, Feb. 2009, 37(3):731-737, doi: 10.1093/nar/gkn936.

Tse-Dinh, Y.-C., "Targeting Bacterial Topoisomerase I to Meet the Challenge of Finding New Antibiotics." *Future Med. Chem.*, Mar. 2015, 7(4):459-471, doi: 10.4155/fmc.14.157.

Vos, S.M. et al., "All Tangled Up: How Cells Direct, Manage and Exploit Topoisomerase Function." *Molecular Cell Biology*, Dec. 2011, 12:827-841, doi: 10.1038/nrm3228.

Williams, K.J. et al., "Improved Mycobacterial Tetracycline Inducible Vectors." *Plasmid*, Sep. 2010, 64(2):69-73, doi: 10.1016/j.plasmid.2010.04.003.

Wu, J. et al., "Scaffold Ranking and Positional Scanning Utilized in the Discovery of nAChR-Selective Compounds Suitable for Optimization Studies." *J. Med. Chem.*, Nov. 2013, 56:10103-10117, doi: 10.1021/jm401543h.

Yamaguchi, Y., Inouye, M., "An Endogenous Protein Inhibitor, YjhX (TopAl), for Topoisomerase I from *Escherichia coli.*" *Nucleic Acids Research*, Nov. 2015, 43(21):10387-10396, doi: 10.1093/nar/gkv1197.

Yigit, H., Reznikoff, W.S., "*Escherichia coli* DNA Topoisomerase I and Suppression of Killing by Tn5 Transposase Overproduction: Topoisomerase I Modulates Tn5 Transposition." *Journal of Bacteriology*, Nov. 1998, 181(22):5866-5874.

Yigit, H., Reznikoff, W.S., "*Escherichia coli* DNA Topoisomerase I Copurifies with Tn5 Transposase, and Tn5 Transposase Inhibits Topoisomerase I." *Journal of Bacteriology*, May 1999, 181(10):3185-3192.

Zhang, Z. et al., "Crystal Structure of a Covalent Intermediate in DNA Cleavage and Rejoining by *Escherichia coli* DNA Topoisomerase I." *PNAS*, Apr. 2011, 108(17):6939-6944, doi: 10.1073/pnas.1100300108.

* cited by examiner

BACTERIAL TOPOISOMERASE INHIBITORS AND USE THEREOF

CROSS-REFERENCE TO A RELATED APPLICATION

This application claims the benefit of U.S. provisional application Ser. No. 62/324,772, filed Apr. 19, 2016, which is incorporated herein by reference in its entirety.

GOVERNMENT SUPPORT

This invention was made with government support under AI069313 awarded by the National Institutes of Health. The government has certain rights in the invention.

BACKGROUND OF INVENTION

Microbial pathogens are becoming increasingly resistant to current antibiotics, limiting the availability of clinical treatment options for bacterial infections (1). It is imperative to develop novel classes of antibacterial compounds, preferably against a new target to avoid cross-resistance. Tuberculosis (TB) infects 9.6 million people a year and causes 1.5 million deaths each year (2). The problem presented by multi-drug resistance is illustrated by the 480,000 cases of multi-drug resistant TB (MDR-TB) that do not respond to first line treatment drugs, with around ten percent of these cases being extensively-drug resistant tuberculosis (XDR-TB) that are resistant to even some of the second line drugs (2, 3). New combinations of anti-TB drugs are needed to treat the MDR-TB and XDR-TB cases.

Topoisomerases are needed in every organism to regulate DNA topology so that vital cellular processes including DNA replication, transcription, recombination and repair can proceed without hindrance (4, 5). Type IIA topoisomerases cut and rejoin a double strand of DNA during catalysis (6). DNA gyrase and topoisomerase IV are prokaryotic type IIA topoisomerases that have been extensively explored as validated targets for antibacterial therapy in the clinic (7, 8). At least one type IA topoisomerase is present in every bacterial pathogen to resolve topological barriers that require the cutting and rejoining of a single strand of DNA and passage of DNA through the transient break (9). Topoisomerase I is the major type IA topoisomerase activity responsible for preventing excessive negative supercoiling in bacteria (10, 11). Bacterial topoisomerase I has received some recent interests as a novel antibacterial drug target (9, 12). *Escherichia coli* topoisomerase I (EcTopI) is the most extensively studied type IA topoisomerase, with crystal structures of covalent cleavage complex (13) and full-length enzyme-DNA complex (14) available. Inhibition of EcTopI by endogenous polypeptide inhibitors (15-17) can lead to cell killing even though compensatory mutations could allow *E. coli* strains with topA deletion to be viable (18, 19). There is also evidence that topoisomerase I function is essential for a number of bacterial pathogens including *Streptococcus pneumoniae* (20) and *Helicobacter pylori* (21). There is only one type IA topoisomerase encoded by the genomes of Mycobacteria. *Mycobacterium tuberculosis* topoisomerase I (MtbTop1) has been demonstrated in genetic studies to be essential for viability both in vitro (22, 23) and in vivo (23). Experimental data showed that the minimal inhibitory concentrations (MICs) of select small molecules against *Mycobacterium tuberculosis* can be shifted by overexpression of topoisomerase I (23, 24), further validating topoisomerase I as a vulnerable target in *M. tuberculosis* for chemical inhibition.

Many of the small molecules identified previously as bacterial topoisomerase I inhibitors are DNA intercalators (20, 24-26) or minor groove binders (27, 28) that would not be attractive candidates for antibiotics development. Therefore, there is an urgent need to develop compounds that target bacterial pathogen, in particular, through the inhibition of bacterial topoisomerase I.

BRIEF SUMMARY

The current invention provides compounds and methods for inhibiting the activity of topoisomerase. These compounds and methods according to the current invention can further be used against bacterial pathogens. The current invention also provides pharmaceutical compositions comprising one or more compounds, and methods comprising administering the composition for treating subjects infected with bacterial pathogens.

In one embodiment, the compound comprises a polyamine scaffold. The scaffold comprises one or more amine groups in the core structure. The amine groups can be primary, secondary, tertiary amines, or a combination thereof. The scaffold also contains one or more R groups, e.g. $R^1$, $R^2$ . . . and $R^n$ ($n \geq 1$), which are independent from each other.

In one embodiment, the compound has a general structure as:

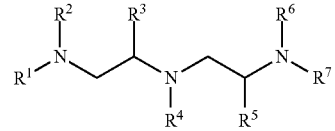

wherein $R^1$, $R^2$, $R^3$, $R^4$, $R^5$, $R^6$, and $R^7$ are each independently selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, haloalkyl, acyl, amino, alkylamino, hydroxyl, hydroxylalkyl, thiol and —COOH.

In a further embodiment, $R^1$, $R^2$, $R^4$, and $R^6$, are hydrogen. In another embodiment, at least one of $R^3$ and $R^5$ comprises an alpha amino acid side chain. These alpha amino acid side chains result from exhaustive reduction. In certain embodiments, at least one of $R^3$ and $R^5$ comprises an alkyl amino group such as di-methyl amino group. In a specific embodiment, at least one of $R^3$, $R^5$, and $R^7$ comprises an alkyl naphthyl group, such as a methyl or ethyl naphthyl group.

In one embodiment, the compound has a general structure as:

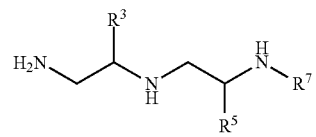

wherein $R^3$, $R^5$, and $R^7$ are independent hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, amino, alkylamino, hydroxyl, hydroxylalkyl, alkenyl, alkynyl, haloalkyl, thiol or —COOH. In a specific embodiment, each of $R^3$ and $R^5$ comprises a positively charged functional group or a large aromatic, and $R^7$ comprises an alkyl naphthyl group, such as a methyl naphthyl group.

In one embodiment, the compound has a general structure selected from:

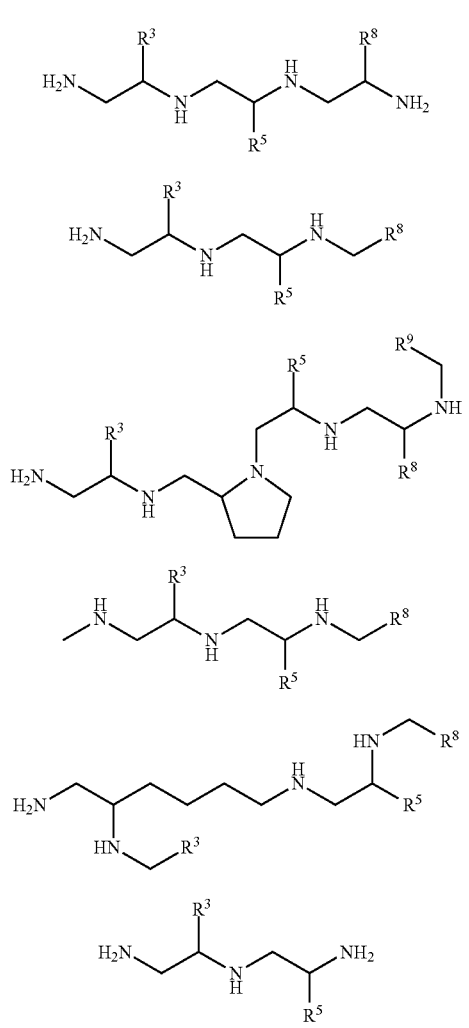

wherein $R^3$, $R^5$, $R^8$, and $R^9$ are each independently selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, haloalkyl, thiol, acyl, amino, alkylamino, hydroxyl, hydroxylalkyl, and —COOH, and wherein 1456, 2229, 1952, 1665, 2161, and 2227 are each independent compound libraries.

In a further embodiment, each of $R^3$, $R^5$, $R^8$, and $R^9$ comprises an alpha amino acid side chain. Specifically, each of $R^3$, $R^5$, $R^8$, and $R^9$ comprises are simple aliphatic amino acid side chain.

In one embodiment, $R^3$, $R^5$, $R^8$, and $R^9$ each independently, comprises positively charged functional groups or large aromatics. In a specific embodiment, at least one of $R^3$, $R^5$, $R^8$, and $R^9$ comprises a naphthyl group, preferably, an alkyl naphthyl group, such as a methyl or ethyl naphthyl group.

In another embodiment, $R^3$, $R^5$, $R^8$, and $R^9$, each independently, comprises an alkyl amino group such as a di-methyl amino group. In a specific embodiment, $R^3$ and $R^5$ contain positively charged functional groups or large aromatics and $R^8$ contains a naphthyl group.

In one embodiment, the compound has a general structure selected from:

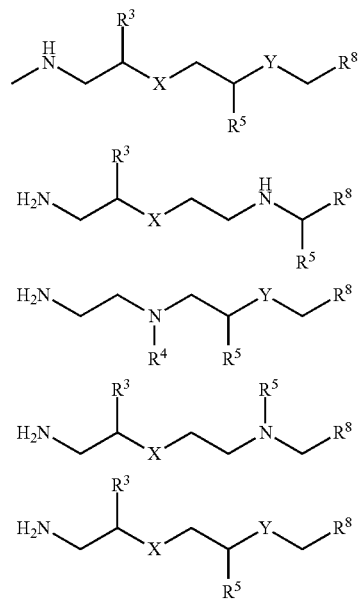

wherein each of X and Y is an independent primary, secondary or tertiary amines, preferably, —NH, —NMe, —NAc, or —NCH$_2$CH$_2$N, and $R^3$, $R^4$, $R^5$, $R^6$, and $R^8$ are each independently selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, haloalkyl, thiol, acyl, amino, alkylamino, hydroxyl, hydroxylalkyl, and —COOH, In one embodiment, each of $R^1$, $R^2$, $R^3$, $R^4$, $R^5$, $R^6$, $R^7$, $R^8$ and $R^9$ is selected from

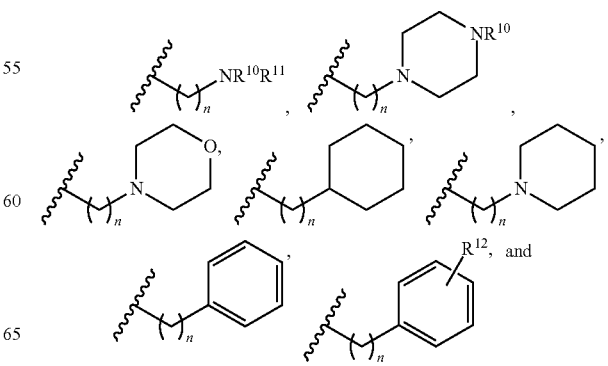

-continued

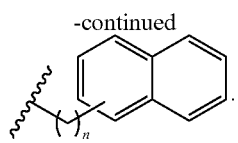

wherein n is at least 2, preferably, ranging from 2 to 5, and $R^{10}$, $R^{11}$, and $R^{12}$ are each independently selected from the group consisting of hydrogen, alkyl, substituted alkyl, aryl, substituted aryl, heteroaryl, substituted heteroaryl, cycloalkyl, substituted cycloalkyl, cycloalkenyl, and substituted cycloalkenyl, alkenyl, alkynyl, haloalkyl, thiol, acyl, amino, alkylamino, hydroxyl, hydroxylalkyl, and —COOH. Preferably, each of $R^{10}$ and $R^{11}$ is an H or an alkyl group.

In a specific embodiment, $R^8$ is a carboxylic acid, or selected from:

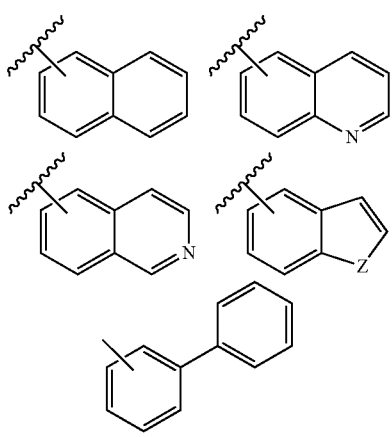

wherein Z is preferably O, NH, NMe, or S. In another embodiment, at least one of $R^3$, $R^5$ and $R^8$ comprises an alkyl amino group such as a di-methyl amino group.

In one embodiment, the compounds in library 2471 are derived from library 2229 and synthesized from the same polyamine scaffold.

In one embodiment, the compounds have activity against bacterial pathogens, including both gram-positive and -negative bacteria. In a further embodiment, the compounds have activity against mycobacteria. In another further embodiment, the compounds have activity against *E. coli, Staphylococcus aureus, Streptococcus pneumoniae, Helicobacter pylori, Enterococcus faecalis, Mycobacterium smegmatis* or *Mycobacterium tuberculosis*. In a preferred embodiment, the compounds have activity against *M. tuberculosis* and pulmonary non-tuberculosis mycobacteria (NTM), such as *Mycobacterium avium* and *Mycobacterium abscessus*.

In another embodiment, the compounds have activity against drug resistant bacterial pathogens, preferably, *M. tuberculosis* and *Staphylococcus aureus*. In another embodiment, the compounds have activity against drug resistant biofilms formed by bacterial pathogens such as non-tuberculosis mycobacteria (NTM).

In one embodiment, the compounds inhibit the activity of topoisomerase, preferably, the type IA family of topoisomerase, more preferably, bacterial topoisomerase I. Additionally, the compounds exhibit selective inhibition of bacterial topoisomerase I over DNA gyrase.

In one embodiment, the compounds target bacterial pathogens through the inhibition of topoisomerase. In a further embodiment, the compounds inhibit the growth of bacterial pathogens by targeting the type IA family of topoisomerase. In a preferred embodiment, the compounds exhibit cytotoxicity by inhibiting bacterial topoisomerase I. In a more preferred embodiment, the compounds inhibit *M. tuberculosis* topoisomerase I (MtbTopI).

In one embodiment, the compounds are bactericidal against bacterial pathogens, including both gram-positive and -negative bacteria. The compounds are effective in eliminating bacterial pathogens under all growth condition. In a further embodiment, the compounds are bactericidal against mycobacteria. In another further embodiment, the compounds are bactericidal against *E. coli, Staphylococcus aureus, Streptococcus pneumoniae, Helicobacter pylori, M. smegmatis*, NTM, such as *Mycobacterium avium* and *Mycobacterium abscessus*. or *M. tuberculosis*, preferably, *M. tuberculosis*.

In another embodiment, the compounds are bactericidal against drug resistant bacterial pathogens, preferably, *M. tuberculosis* and *Staphylococcus aureus*. In another embodiment, the compounds have activity against drug resistant biofilms formed by bacterial pathogens such as NTM.

In one embodiment, the compounds are used as antibacterial drugs in antibacterial therapy. In a specific embodiment, the compounds are used in treatment of infectious diseases, preferably, Tuberculosis.

In one embodiment, the compounds can be used as antituberculusis agents.

In one embodiment, the current invention provides a pharmaceutical composition comprising one or more compounds. The composition further comprises a pharmaceutically acceptable carrier.

In a further embodiment, the compounds are in a pharmaceutically acceptable salt form or a form of free base. The composition may further contain pharmaceutically acceptable ingredients including metal salts and/or buffers. In certain embodiments, the pharmaceutical compositions can also include additional pharmaceutical active compounds know in the art.

In one embodiment, the current invention provides a pharmaceutical composition for treating conditions involving bacterial infection, preferably Tuberculosis.

In one embodiment, the current invention also provides a method for treating a bacterial infection in a subject, comprising administering an effective amount of the pharmaceutical composition comprising one or more compounds according to the subject invention, to a subject in need of such treatment. In a preferred embodiment, the subject is a human.

In another preferred embodiment, the human patient is infected with *M. tuberculosis*.

In one embodiment, the current invention provides a method for treating Tuberculosis, preferably, drug resistant Tuberculosis.

In one embodiment, the effective amount of the pharmaceutical composition can be administered through oral, rectal, bronchial, nasal, topical, buccal, sub-lingual, transdermal, vaginal, intramuscular, intraperitoneal, intravenous, intra-arterial, intracerebral, interaocular administration.

The present invention also provides a method for inhibiting a topoisomerase in a subject, comprising administering, to the subject, an effective amount of one or more compounds. In a preferred embodiment, the subject is a human or a bacterium.

The present invention also provides a method for inhibiting type IA topoisomerase in a subject, preferably in a human or a bacterium, comprising administering an effective amount of one or more compounds to the subject.

The present invention also provides a kit comprising the compounds or pharmaceutical compositions as described herein.

The compounds, compositions, methods and kits described herein can be used in connection with pharmaceutical, medical, veterinary, and disinfection applications, as well as fundamental biological research and methodologies, as would be identified by a skilled person upon reading of the present disclosure.

DETAILED DISCLOSURE

Figure 1A:
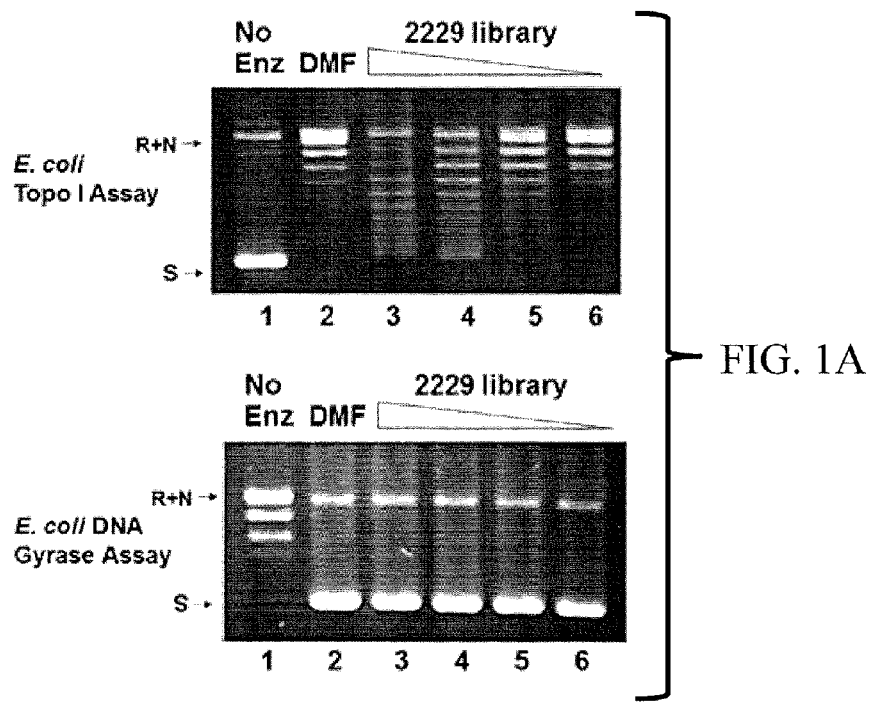
FIGS. 1A-1B Inhibition of *E. coli* topoisomerase I relaxation activity by scaffold ranking library 2229. (1A) Scaffold library mixture 2229 inhibits *E. coli* topoisomerase I but not DNA gyrase. Lane 1: Control reaction with no enzyme added: lane 2: Enzyme with DMF control; Lanes 3-6: Enzyme with scaffold library mixture 2229 at concentrations of 100, 50, 25, 12.5 μg/mL. (1B) Polyamine scaffolds among the 50 scaffold ranking library mixtures tested at 100 μg/mL for inhibition of *E. coli* topoisomerase I. Only library 2229 showed inhibition of the relaxation activity.

The current invention provides compounds and methods for inhibiting the activity of topoisomerase. The compounds according to the invention have activity against one or more bacterial pathogens. The current invention also provides a pharmaceutical composition comprising at least one of the compounds, and methods comprising administering of the compositions for treating a subject infected with a bacterial pathogen or in need of such administration for inhibiting the activity of topoisomerase.

In one embodiment, the compounds comprise a polyamine scaffold. In a specific embodiment, the polyamine scaffold comprises one or more amine groups in the core structure. The amine groups may be primary, secondary, tertiary amines, or a combination thereof. The polyamine scaffold also contains one or more R groups, e.g. $R^1$, $R^2$ ... and $R^n$ ($n \geq 1$), which are independent of each other.

In one embodiment, the compound has a general structure as:

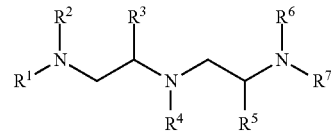

wherein $R^1$, $R^2$, $R^3$, $R^4$, $R^5$, $R^6$, and $R^7$ are each independently selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, substituted cycloalkenyl, alkenyl, alkynyl, thiol, haloalkyl, acyl, amino, alkylamino, hydroxyl, hydroxylalkyl, and —COOH.

As used herein, "alkyl" means linear saturated monovalent radicals of at least one carbon atom or a branched saturated monovalent of at least three carbon atoms. It may include hydrocarbon radicals of at least one carbon atom, which may be linear. Examples include, but not limited to, methyl, ethyl, propyl, 2-propyl, n-butyl, iso-butyl, tert-butyl, pentyl, hexyl, and the like.

As used herein, "acyl" means a radical —C(O)R where R includes, but not limited to, hydrogen, alkyl or cycloalkyl, and heterocycloalkyl. Examples include, but not limited to, formyl, acetyl, ethylcarbonyl, and the like. An aryl group may be substituted or unsubstituted.

As used herein, "alkylamino" means a radical —NHR or —NR2 where each R is, independently, an alkyl group. Examples include, but not limited to, methylamino, (1-methylethyl)amino, dimethyl amino, methylethylamino, di(1-methylethyl)amino, and the like. An alkylamino may be substituted or unsubstituted.

As used herein, "hydroxyalkyl" means an alkyl radical substituted with one or more hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl. A hydroxyalkyl may be substituted or unsubstituted.

As used herein, "alkenyl" refers to a straight or branched hydrocarbon chain containing one or more double bonds. The alkenyl group may have 2 to 9 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. The alkynyl group may have 2 to 9 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "C2-4 alkynyl" or similar designations. By way of example only, "C2-4alkynyl" indicates that there are two to four carbon atoms in the alkynyl chain, i.e., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclyl ring or ring system. Examples include, but are not limited to, cyclopropyl, cyclobutyl, cyclopentyl, and cyclohexyl.

As used herein, "aryl" refers to a carbocyclic (all carbon) monocyclic or multicyclic aromatic ring system (including fused ring systems where two carbocyclic rings share a chemical bond). The number of carbon atoms in an aryl group can vary. For example, the aryl group can be a C6-C14 aryl group, a C6-C10 aryl group, or a C6 aryl group. Examples of aryl groups include, but are not limited to, phenyl, benzyl, α-naphthyl, β-naphthyl, biphenyl, anthryl, tetrahydronaphthyl, fluorenyl, indanyl, biphenylenyl, and acenaphthenyl. Preferred aryl groups are phenyl and naphthyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "substituted" group may be substituted with one or more group(s) individually and independently selected from alkyl, alkenyl, alkynyl, cycloalkyl, cycloalkenyl, cycloalkynyl, benzyl, substituted benzyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiol, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

In one embodiment, at least one of $R^1$, $R^2$, $R^3$, $R^4$, $R^5$, $R^6$, and $R^7$ comprises an alpha amino acid side chain. These alpha amino acid side chains result from exhaustive reduction. Preferably, at least one of $R^3$ and $R^5$ comprises an alpha amino acid side chain. In a further embodiment, $R^1$, $R^2$, $R^3$, $R^4$, $R^5$, $R^6$, and $R^7$ may each independently comprise a positively charged functional group or a large aromatic. Specifically, $R^1$, $R^2$, $R^3$, $R^4$, $R^5$, $R^6$, and $R^7$ may each independently comprise a naphthyl group.

In another embodiment, $R^1$, $R^2$, $R^4$, and $R^6$, are independent hydrogens. $R^3$, $R^5$, and $R^7$ are each independently selected from hydrogen, alkyl, substituted alkyl including benzyl and substituted benzyl, alkenyl, alkynyl, thiol, haloalkyl, acyl, amino, alkylamino, hydroxyl, hydroxylalkyl, and —COOH.

In a further embodiment, each of $R^3$, $R^5$, and $R^7$ independently comprises an alkylamino group such as a di-methyl amino group. In a specific embodiment, each of $R^3$, $R^5$, and $R^7$ independently comprises an alkyl naphthyl group, such as a methyl or ethyl naphthyl group.

In one embodiment, the compound has a general structure as:

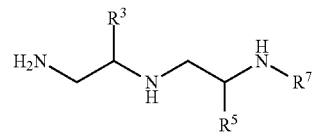

wherein $R^3$, $R^5$, and $R^7$ are each independently selected from hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, thiol, haloalkyl, acyl, amino, alkylamino, hydroxyl, hydroxylalkyl, and —COOH.

In another embodiment, each of $R^3$ and $R^5$ independently comprises a positively charged functional group or a large aromatic. In a further embodiment, at least one of $R^3$, $R^5$, and $R^7$ comprises an alkylamino group such as a di-methyl amino group. In a specific embodiment, at least one of $R^3$, $R^5$, and $R^7$ comprises an alkyl naphthyl group, such as a methyl or ethyl naphthyl group.

In one embodiment, the compound has a general structure selected from below:

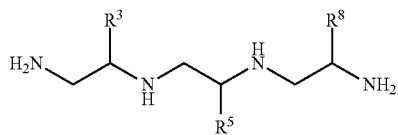

1456

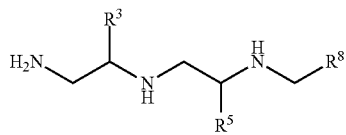

2229

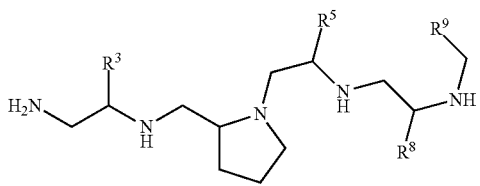

1952

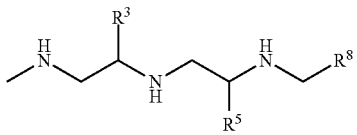

1665

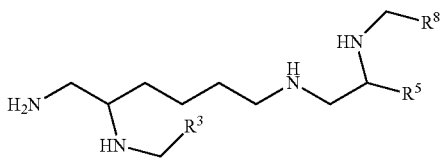

2161

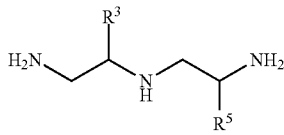

2227 wherein R³, R⁵, R⁸, and R⁹ are each independently selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, thiol, haloalkyl, acyl, amino, alkylamino, hydroxyl, hydroxylalkyl, and —COOH, and wherein 1456, 2229, 1952, 1665, 2161, and 2227 are each independent compound libraries.

In one embodiment, each of R³, R⁵, R⁸, and R⁹ comprises an independent amino acid side chain. These alpha amino acid side chains result from exhaustive reduction. Preferably, at least one of R³ and R⁵ comprises an alpha amino acid side chain. Specifically, R³ and R⁵ are, each independently, simple aliphatic amino acids. In a specific embodiment, R⁸ is a carboxylic acid.

In one embodiment, R³, R⁵, R⁸, and R⁹ each independently, contains positively charged functional groups or large aromatics. Specifically, R³, R⁵, R⁸, and R⁹ may each independently comprise a naphthyl group. Examples of the naphthyl group include, but are not limited to, dihydroxyphenyl, halogenated phenyls, aliphatic groups. In a specific embodiment, each of R³, R⁵, R⁸, and R⁹ independently comprises an alkyl naphthyl group, such as a methyl or ethyl naphthyl group.

In another embodiment, R³, R⁵, R⁸, and R⁹ each independently, comprises an alkylamino group such as a di-methyl amino group. In a preferred embodiment, R³ and R⁵ contain positively charged functional groups or large aromatics and R⁸ contains a naphthyl group.

In one embodiment, the compound has a general structure as shown below:

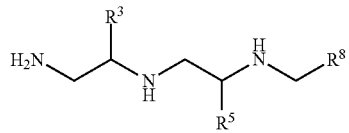

2229 wherein R³, R⁵, and R⁸ are each independently selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, thiol, haloalkyl, acyl, amino, alkylamino, hydroxyl, hydroxylalkyl, and —COOH.

In a further embodiment, each of R³, R⁵, and R⁸ comprises an amino acid side chain. Preferably, at least one of R³ and R⁵ comprises an alpha amino acid side chain. More preferably, at least one of R³ and R⁵ comprises a simple aliphatic amino acid side chain. Specifically, each of R³ and R⁵ independently comprises positively charged functional groups or large aromatics.

In one embodiment, at least one of R³, R⁵, and R⁸, comprises a naphthyl group, preferably, an alkyl naphthyl group, such as a methyl or ethyl naphthyl group. Other naphthyl groups include, but are not limited to, dihydroxyphenyl, halogenated phenyls, aliphatic groups.

In another embodiment, at least one of R³, R⁵, and R⁸ comprises an alkylamino group such as a di-methyl amino group.

In some embodiments, the polyamine scaffolds comprise alkylation and/or acetylation of the primary, secondary and/or tertiary amines.

In one embodiment, the compound has a general structure selected from:

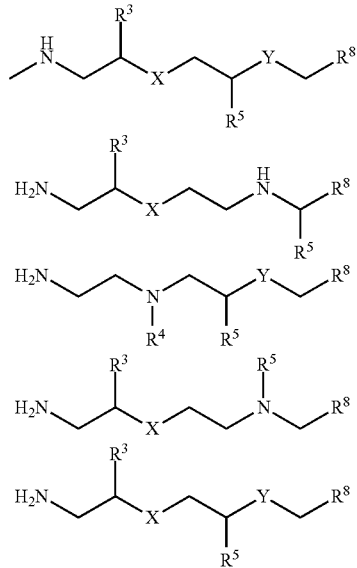

wherein each of X and Y is an independent primary, secondary or tertiary amines, preferably, each of X and Y is independently selected from —NH, —NMe, —NAc, or —NCH$_2$CH$_2$N; and wherein R$^3$, R$^4$, R$^5$, R$^6$, and R$^8$ are each independently selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, thiol, haloalkyl, acyl, amino, alkylamino, hydroxyl, hydroxylalkyl, and —COOH, In another embodiment, each of R$^3$ and R$^5$ is an independent amino acid or selected from:

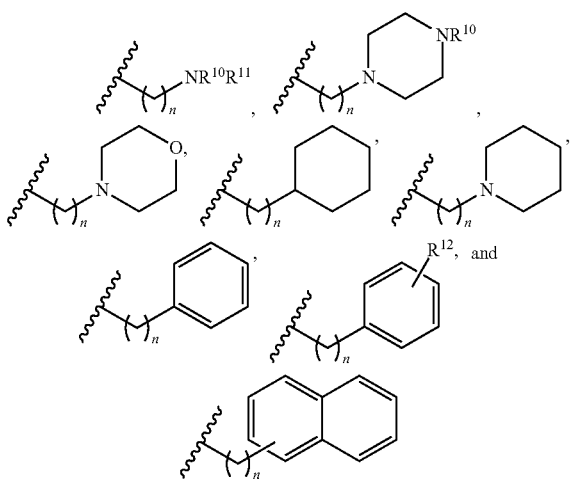

wherein n is at least 2, preferably, ranging from 2 to 5, and R$^{10}$, R$^{11}$, and R$^{12}$ are each independently selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, thiol, haloalkyl, acyl, amino, alkylamino, hydroxyl, hydroxylalkyl, and —COOH. Preferably, each of R$^{10}$ and R$^{11}$ is an H or an alkyl group.

In a specific embodiment, R$^8$ is a carboxylic acid, or selected from:

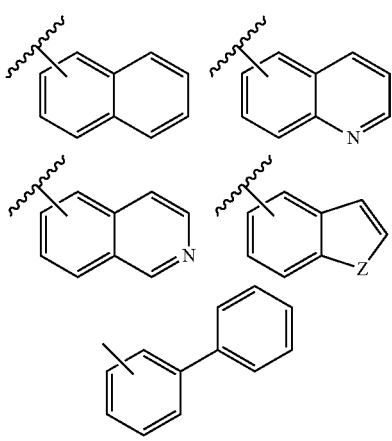

wherein Z is preferably O, NH, NMe, or S.

In a further embodiment, each R group, preferably, R$^3$, R$^5$, and R$^8$ group may comprise other functional groups including quinolones, indoles, benzofurans, benzothiophenes, and biphenyls.

In one embodiment, the R groups including R$^1$, R$^2$ ... and (n≥1) may each independently include alkyl amines with varying chain lengths, cyclic amines (e.g. piperazine, morpholine, piperidine), cyclic alkyls, and aryl groups.

In specific embodiments, the compounds are selected form the molecules listed below in Table 1. These compounds in library 2471 were derived from library 2229 and synthesized from the general structure as shown below:

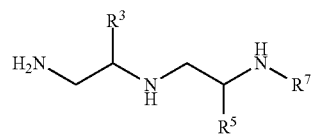

wherein R$^3$, R$^5$, and R$^7$ are each independent groups selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, haloalkyl, acyl, amino, alkylamino, hydroxyl, hydroxylalkyl, thiol, and —COOH. Preferably, at least one of R$^3$ and R$^5$ comprises an amino acid side chain. Specifically, each of R$^3$ and R$^5$, independently, comprises a positively charged functional group or a large aromatic.

In one embodiment, at least one of R$^3$, R$^5$, and R$^7$ comprises a naphthyl group, preferably, an alkyl naphthyl group such as a methyl naphthyl group. The naphthyl group includes, but is not limited to, dihydroxyphenyl, halogenated phenyls, aliphatic groups. In another embodiment, at least one of R$^3$, and R$^5$ comprises an alkyl amino group such as a di-methyl amino group. In a specific embodiment, R$^7$ is a carboxylic acid, or selected from:

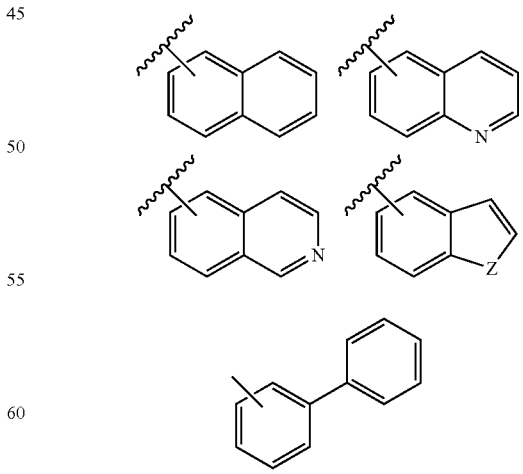

wherein Z is preferably O, NH, NMe, or S.

Specifically, these compounds in library 2471 have a general structure as shown below:

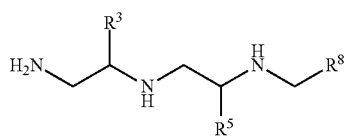

2471 wherein $R^3$, $R^5$, and $R^8$ are each independent groups selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkynyl, acyl, thiol, haloalkyl, acyl, amino, alkylamino, hydroxyl, hydroxylalkyl, and —COOH. Preferably, each of $R^3$ and $R^5$ is independent amino acids, and $R^8$ is a carboxylic acid. In a preferred embodiment, $R^3$ and $R^5$ comprise positively charged functional groups or large aromatics. In another preferred embodiment, $R^8$ comprises a naphthyl group (i.e. dihydroxyphenyl, halogenated phenyls, aliphatic groups, etc.). In a specific embodiment, $R^8$ comprises a naphthyl group, preferably, an alkyl naphthyl group, such as a methyl naphthyl group.

TABLE 1

Information on 80 individual compounds synthesized: $R^3$, $R^5$, $R^8$ substitutions and $IC_{50}$ values for inhibition of E. coli topoisomerase I relaxation activity

| COMPOUND # | R3 | R5 | R8 | EcTopI relaxation inhibition ($IC_{50}$, μM) |
|---|---|---|---|---|
| 2471-18 | S-3-aminopropyl | S-3-guanidinepropyl | 1-naphthylmethyl | 1.2 |
| 2471-27 | R-4-(methylamino)butyl | S-4-(methylamino)butyl | 1-naphthylmethyl | 1.2 |
| 2471-15 | S-3-aminopropyl | S-4-(methylamino)butyl | 1-naphthylmethyl | 1.9 |
| 2471-3 | S-4-(methylamino)butyl | S-4-(methylamino)butyl | 1-naphthylmethyl | 2.5 |
| 2471-6 | S-4-(methylamino)butyl | S-3-guanidinepropyl | 1-naphthylmethyl | 2.5 |
| 2471-30 | R-4-(methylamino)butyl | S-3-guanidinepropyl | 1-naphthylmethyl | 2.5 |
| 2471-80 | S-2-naphthylmethyl | S-3-(methylamino)propyl | 1-naphthylethyl | 2.5 |
| 2471-9 | S-4-(methylamino)butyl | R-propyl | 1-naphthylmethyl | 5 |
| 2471-33 | R-4-(methylamino)butyl | R-propyl | 1-naphthylmethyl | 5 |
| 2471-12 | S-4-(methylamino)butyl | S-butyl | 1-naphthylmethyl | 7.5 |
| 2471-21 | S-3-aminopropyl | R-propyl | 1-naphthylmethyl | 7.5 |
| 2471-24 | S-3-aminopropyl | S-butyl | 1-naphthylmethyl | 10 |
| 2471-36 | R-4-(methylamino)butyl | S-butyl | 1-naphthylmethyl | 20 |
| 2471-76 | R-2-(1H-indol-3-yl)ethyl | S-3-(methylamino)propyl | 1-naphthylethyl | 20 |
| 2471-79 | S-2-naphthylmethyl | S-3-(methylamino)propyl | 2-(3,4-dichloro-phenyl)-ethyl | 30 |
| 2471-16 | S-3-aminopropyl | S-3-guanidinepropyl | 2-(3-bromo-phenyl)-ethyl | 40 |
| | R-4-(methylamino)butyl | S-3-guanidinepropyl | 2-(3-bromo-phenyl)-ethyl | |
| 2471-37 | S-2-naphthylmethyl | R-butyl | 2-(3,5-Bis(Trifluoromethyl)phenyl)-ethyl | 40 |
| 2471-38 | S-2-naphthylmethyl | R-butyl | 4-tert-butyl-cyclohexyl | 40 |
| 2471-39 | S-2-naphthylmethyl | R-butyl | 4-Cyclohexylbutyl | 40 |
| 2471-40 | S-2-naphthylmethyl | S-3-(methylamino)propyl | 2-(3,5-Bis(Trifluoromethyl)phenyl)-ethyl | 40 |
| 2471-41 | S-2-naphthylmethyl | S-3-(methylamino)propyl | 4-tert-butyl-cyclohexyl | 40 |
| 2471-42 | S-2-naphthylmethyl | S-3-(methylamino)propyl | 4-Cyclohexylbutyl | 40 |
| 2471-43 | S-2-naphthylmethyl | R-3-(methylamino)propyl | 2-(3,5-Bis(Trifluoromethyl)phenyl)-ethyl | 40 |
| 2471-44 | S-2-naphthylmethyl | R-3-(methylamino)propyl | 4-tert-butyl-cyclohexyl | 40 |
| 2471-45 | S-2-naphthylmethyl | R-3-(methylamino)propyl | 4-Cyclohexylbutyl | 40 |
| 2471-46 | S-2-naphthylmethyl | S-4-fluorobenzyl | 2-(3,5-Bis(Trifluoromethyl)phenyl)-ethyl | 40 |
| 2471-47 | S-2-naphthylmethyl | S-4-fluorobenzyl | 4-tert-butyl-cyclohexyl | 40 |
| 2471-48 | S-2-naphthylmethyl | S-4-fluorobenzyl | 4-Cyclohexylbutyl | 40 |
| 2471-49 | S-cyclohexylmethyl | R-butyl | 2-(3,5-Bis(Trifluoromethyl)phenyl)-ethyl | 40 |
| 2471-58 | S-cyclohexylmethyl | S-4-fluorobenzyl | 2-(3,5-Bis(Trifluoromethyl)phenyl)-ethyl | 40 |
| 2471-59 | S-cyclohexylmethyl | S-4-fluorobenzyl | 4-tert-butyl-cyclohexyl | 40 |
| 2471-60 | S-cyclohexylmethyl | S-4-fluorobenzyl | 4-Cyclohexylbutyl | 40 |
| 2471-61 | R-cyclohexylmethyl | R-butyl | 2-(3,5-Bis(Trifluoromethyl)phenyl)-ethyl | 40 |
| 2471-70 | R-cyclohexylmethyl | S-4-fluorobenzyl | 2-(3,5-Bis(Trifluoromethyl)phenyl)-ethyl | 40 |
| 2471-71 | R-cyclohexylmethyl | S-4-fluorobenzyl | 4-tert-butyl-cyclohexyl | 40 |
| 2471-72 | R-cyclohexylmethyl | S-4-fluorobenzyl | 4-Cyclohexylbutyl | 40 |
| 2471-73 | R-2-(1H-indol-3-yl)ethyl | R-2-(1H-indol-3-yl)ethyl | 2-(3,4-dichloro-phenyl)-ethyl | 40 |
| 2471-74 | R-2-(1H-indol-3-yl)ethyl | R-2-(1H-indol-3-yl)ethyl | 1-naphthylethyl | 40 |
| 2471-77 | S-2-naphthylmethyl | R-2-(1H-indol-3-yl)ethyl | 2-(3,4-dichloro-phenyl)-ethyl | 40 |

TABLE 1-continued

Information on 80 individual compounds synthesized: $R^3$, $R^5$, $R^8$ substitutions and $IC_{50}$ values for inhibition of E. coli topoisomerase I relaxation activity

| COMPOUND # | R3 | R5 | R8 | EcTopI relaxation inhibition ($IC_{50}$, µM) |
|---|---|---|---|---|
| 2471-78 | S-2-naphthylmethyl | R-2-(1H-indol-3-yl)ethyl | 1-naphthylethyl | 40 |
| 2471-26 | R-4-(methylamino)butyl | S-4-(methylamino)butyl | 2-(3,4-dihydroxy-phenyl)-ethyl | 80 |
| 2471-69 | R-cyclohexylmethyl | R-3-(methylamino)propyl | 4-Cyclohexylbutyl | 80 |
| 2471-75 | R-2-(1H-indol-3-yl)ethyl | S-3-(methylamino)propyl | 2-(3,4-dichloro-phenyl)-ethyl | 80 |
| 2471-2 | S-4-(methylamino)butyl | S-4-(methylamino)butyl | 2-(3,4-dihydroxy-phenyl)-ethyl | 120 |
| 2471-29 | R-4-(methylamino)butyl | S-3-guanidinepropyl | 2-(3,4-dihydroxy-phenyl)-ethyl | 120 |
| 2471-1 | S-4-(methylamino)butyl | S-4-(methylamino)butyl | 2-(3-bromo-phenyl)-ethyl | 160 |
| 2471-4 | S-4-(methylamino)butyl | S-3-guanidinepropyl | 2-(3-bromo-phenyl)-ethyl | 160 |
| 2471-7 | S-4-(methylamino)butyl | R-propyl | 2-(3-bromo-phenyl)-ethyl | 160 |
| 2471-10 | S-4-(methylamino)butyl | S-butyl | 2-(3-bromo-phenyl)-ethyl | 160 |
| 2471-13 | S-3-aminopropyl | S-4-(methylamino)butyl | 2-(3-bromo-phenyl)-ethyl | 160 |
| 2471-19 | S-3-aminopropyl | R-propyl | 2-(3-bromo-phenyl)-ethyl | 160 |
| 2471-22 | S-3-aminopropyl | S-butyl | 2-(3-bromo-phenyl)-ethyl | 160 |
| 2471-25 | R-4-(methylamino)butyl | S-4-(methylamino)butyl | 2-(3-bromo-phenyl)-ethyl | 160 |
| 2471-31 | R-4-(methylamino)butyl | R-propyl | 2-(3-bromo-phenyl)-ethyl | 160 |
| 2471-34 | R-4-(methylamino)butyl | S-butyl | 2-(3-bromo-phenyl)-ethyl | 160 |
| 2471-50 | S-cyclohexylmethyl | R-butyl | 4-tert-butyl-cyclohexyl | 160 |
| 2471-51 | S-cyclohexylmethyl | R-butyl | 4-Cyclohexylbutyl | 160 |
| 2471-52 | S-cyclohexylmethyl | S-3-(methylamino)propyl | 2-(3,5-Bis(Trifluoromethyl)phenyl)-ethyl | 160 |
| 2471-55 | S-cyclohexylmethyl | R-3-(methylamino)propyl | 2-(3,5-Bis(Trifluoromethyl)phenyl)-ethyl | 160 |
| 2471-56 | S-cyclohexylmethyl | R-3-(methylamino)propyl | 4-tert-butyl-cyclohexyl | 160 |
| 2471-57 | S-cyclohexylmethyl | R-3-(methylamino)propyl | 4-Cyclohexylbutyl | 160 |
| 2471-62 | R-cyclohexylmethyl | R-butyl | 4-tert-butyl-cyclohexyl | 160 |
| 2471-63 | R-cyclohexylmethyl | R-butyl | 4-Cyclohexylbutyl | 160 |
| 2471-64 | R-cyclohexylmethyl | S-3-(methylamino)propyl | 2-(3,5-Bis(Trifluoromethyl)phenyl)-ethyl | 160 |
| 2471-65 | R-cyclohexylmethyl | S-3-(methylamino)propyl | 4-tert-butyl-cyclohexyl | 160 |
| 2471-66 | R-cyclohexylmethyl | S-3-(methylamino)propyl | 4-Cyclohexylbutyl | 160 |
| 2471-67 | R-cyclohexylmethyl | R-3-(methylamino)propyl | 2-(3,5-Bis(Trifluoromethyl)phenyl)-ethyl | 160 |
| 2471-68 | R-cyclohexylmethyl | R-3-(methylamino)propyl | 4-tert-butyl-cyclohexyl | 160 |
| 2471-8 | S-4-(methylamino)butyl | R-propyl | 2-(3,4-dihydroxy-phenyl)-ethyl | >160 |
| 2471-20 | S-3-aminopropyl | R-propyl | 2-(3,4-dihydroxy-phenyl)-ethyl | >160 |
| 2471-23 | S-3-aminopropyl | S-butyl | 2-(3,4-dihydroxy-phenyl)-ethyl | >160 |
| 2471-32 | R-4-(methylamino)butyl | R-propyl | 2-(3,4-dihydroxy-phenyl)-ethyl | >160 |
| 2471-35 | R-4-(methylamino)butyl | S-butyl | 2-(3,4-dihydroxy-phenyl)-ethyl | >160 |
| 2471-53 | S-cyclohexylmethyl | S-3-(methylamino)propyl | 4-tert-butyl-cyclohexyl | >160 |
| 2471-54 | S-cyclohexylmethyl | S-3-(methylamino)propyl | 4-Cyclohexylbutyl | >160 |
| 2471-5 | S-4-(methylamino)butyl | S-3-guanidinepropyl | 2-(3,4-dihydroxy-phenyl)-ethyl | >160 |
| 2471-11 | S-4-(methylamino)butyl | S-butyl | 2-(3,4-dihydroxy-phenyl)-ethyl | >160 |
| 2471-14 | S-3-aminopropyl | S-4-(methylamino)butyl | 2-(3,4-dihydroxy-phenyl)-ethyl | >160 |
| 2471-17 | S-3-aminopropyl | S-3-guanidinepropyl | 2-(3,4-dihydroxy-phenyl)-ethyl | >160 |

In a specific embodiment, the compounds according to the current invention are selected from: 2471-18, 2471-27, 2471-15, 2471-3, 2471-6, 2471-30, 2471-80, 2471-9, 2471-33, 2471-12, 2471-21, 2471-24, 2471-36, and 2471-76. Preferably, the compounds are selected from 2471-12, 2471-24, 2471-36, and 2471-80.

In one embodiment, these compounds according to the subject invention are from the library 2580 which is derived from library 2229 and synthesized from the same general structure as shown below:

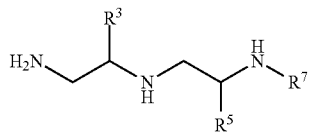

wherein $R^3$, $R^5$, and $R^7$ are each independent groups selected from the group consisting of hydrogen, alkyl, substituted alkyl including benzyl and substituted benzyl, aryl, substituted aryl, heteroaryl, substituted heteroaryl, cycloalkyl, substituted cycloalkyl, cycloalkenyl, and substituted cycloalkenyl, alkenyl, alkynyl, thiol, haloalkyl, acyl, amino, alkylamino, hydroxyl, hydroxylalkyl, and —COOH.

In some embodiments, each of $R^3$, $R^5$, and $R^7$ independently comprises a positively charged functional group or a large aromatic. In a specific embodiment, at least one of $R^3$ and $R^5$, comprises an alkyl amino group such as a di-methyl amino group. In a specific embodiment, at least one of $R^3$, $R^5$, and $R^7$ comprises a naphthyl group, preferably, an alkyl naphthyl group, such as a methyl or ethyl naphthyl group.

In a specific embodiment, the compound is selected form the molecule 2580-3, 2580-15, 2580-18, 2580-24, 2580-27, and 2580-33 as listed below:

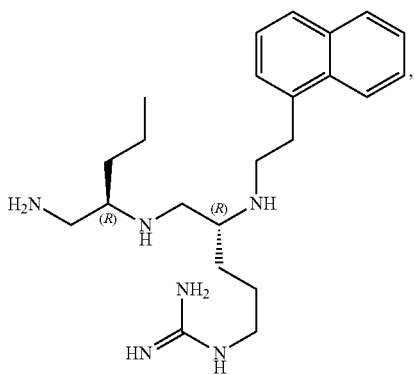

2580-3

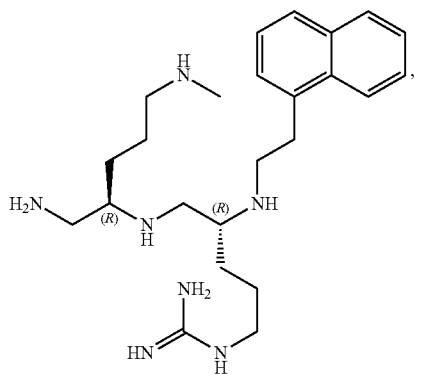

2580-15

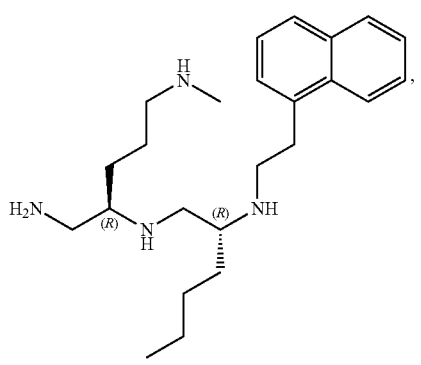

2580-18

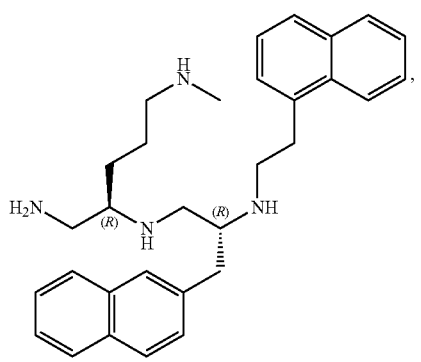

2580-24

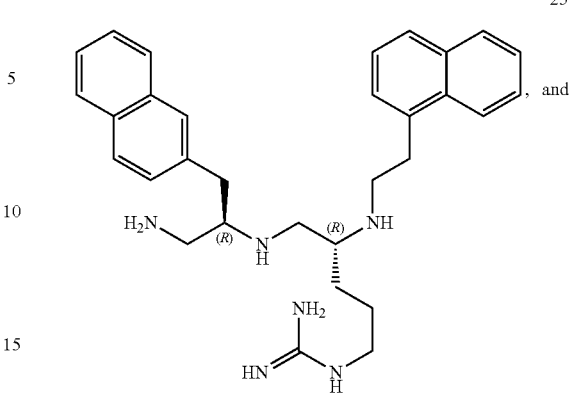

2580-27

2580-33

Specifically, the molecule 2580-3 has a molecular weight of 398.59; 2580-15 has a molecular weight of 427.63; 2580-18 has a molecular weight of 384.60; 2580-24 has a molecular weight of 468.68; 2580-27 has a molecular weight of 496.69; and 2580-33 has a molecular weight of 468.68.

In one embodiment, the compounds can occur as racemates and racemic mixtures, single enantiomer, individual diastereomer, diastereomeric mixtures, and cis-or trans-isomeric forms. The compounds can also be dextrorotary (D) or levorotary (L). Additionally, each chiral center may be in (S)- or (R)-form. Thus, it should be understood by those skilled in the art that the various forms of the compounds of the present invention would be encompassed by the present invention.

In one embodiment, the compounds according to the current invention target topoisomerase, preferably, bacterial topoisomerase, more preferably bacterial topoisomerase in the IA family, and most preferably, bacterial topoisomerase I such as EcTopI and MtbTopI.

In a further embodiment, the compounds inhibit the activity of topoisomerase, preferably, the type IA family of topoisomerase, more preferably, bacterial topoisomerase I such as EcTopI and MtbTopI. Additionally, the compounds exhibit selective inhibition of bacterial topoisomerase I over DNA gyrase.

Advantageously, the compounds inhibit the relaxation activity of EcTopI with $IC_{50}$ values of at least 0.02 µM, preferably, 0.5-160 µM, and more preferably, 0.5-20 µM. In a specific embodiment, the compounds with simple aliphatic substitutions at $R^3$ inhibit the relaxation activity of EcTopI with $IC_{50}$ values greater than 100 µM. However, the compounds with positively charged functional groups or large aromatics at $R^3$ inhibit the relaxation activity of EcTopI with IC$_{50}$ values in the low μM range. Furthermore, the compounds with a naphthyl group at the R$^7$ position inhibit the relaxation activity of EcTopI with IC$_{50}$ values at 20 μM or less.

In one embodiment, the compounds have activity against bacterial pathogens. Bacteria include at least 11 distinct groups as follows: (1) Gram-positive (gram+) bacteria, of which there are two major subdivisions: (i) high G+C group (Actinomycetes, Mycobacteria, *Micrococcus*, others) (ii) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) *Chlamydia*; (8) Green sulfur bacteria; (9) Green nonsulfur bacteria (also anaerobic phototrophs); (10) Radioresistant Inicrococci and relatives; and (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram-positive bacteria" include cocci, nonsporulating rods, and sporulating rods. The genera of Gram-positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

In a further embodiment, the compounds have activity against mycobacteria. In another further embodiment, the compounds have activity against *E. coli, Staphylococcus aureus, Streptococcus pneumoniae, Bacillus subtilis, Bacillus pumilus, Bacillus cereus, Acinetobacter baumanii, Helicobacter pylori, M. smegmatis* and *M. tuberculosis*, preferably, *M. tuberculosis*.

In another embodiment, the compounds have activity against drug resistant bacterial pathogens, preferably, *M. tuberculosis* and *Staphylococcus aureus*. In another embodiment, the compounds have activity against drug resistant biofilms formed by bacterial pathogens such as NTM.

In one embodiment, the compounds inhibit the growth of bacterial pathogens, preferably, through the inhibition of topoisomerase, more preferably, through the inhibition of the type IA family of topoisomerase. In a preferred embodiment, the compounds are bactericidal by inhibiting bacterial topoisomerase I, preferably, MtbTopI.

In specific embodiments, the compounds inhibit the growth of bacteria with IC$_{50}$ values of 100 μM or less, preferably, 20 μM or less, more preferably, 10 μM or less. The growth inhibition IC$_{50}$ refers to the minimum compound concentration that inhibits the growth of bacteria, preferably, growth of *M. tuberculosis*, in comparison to a control in the absence of any compounds by 50%.

In one embodiment, the compounds act as the inhibitor of bacterial topoisomerase, preferably, topoisomerase I by interacting with the enzyme alone to prevent DNA binding or by interacting with the enzyme-DNA complex to inhibit enzyme function and/or DNA cleavage and/or DNA religation. In a further embodiment, the compounds also target bacterial topoisomerase I with different substitutions/mutations located in the conserved or non-conserved sequences or motif. In a preferred embodiment, the compounds bind to the enzyme-DNA complex to form a drug-enzyme-DNA ternary structure.

In certain embodiments, the compounds exhibit antibacterial activity by perturbing the interaction of bacterial topoisomerase I, in particular, EcTopI and MtbTopI with other cellular components such as RNA polymerase, which further leads to increased susceptibility to antibacterial compounds, and reduced tolerance to challenges such as high temperature, acids, and oxidative stress.

In one embodiment, other combinations in the substitutions of R$^1$, R$^2$, R$^3$ . . . and/or (n≥1) on the polyamine scaffold have the possibility of having antimycobacterial activity with mechanisms not related to topoisomerase I.

In some embodiments, the compounds may be derived from the polyamine scaffolds or analogs of the polyamine scaffold. The compounds and analogs may display different selectivity, target specificity, binding affinity, cell penetration and retention properties while inhibiting the activity of topoisomerase, preferably, bacterial topoisomerase I, as well as inhibiting the growth of bacteria, preferably, mycobacteria, more preferably, *M. tuberculosis*. The use of mycobacteria strains with different levels of topoisomerase I expression in cell based-assays could be used to complement the enzyme-based assays to identify and optimize other analogues that can target topoisomerase I. The compounds can also be identified with other assays such as multi-stress in vitro dormancy assay and/or luminescent assay.

In one embodiment, the compounds are bactericidal against bacterial pathogens, including both gram-positive and -negative bacteria. The compounds are effective in eliminating bacterial pathogens under all growth condition. In a further embodiment, the compounds are bactericidal against mycobacteria. In another further embodiment, the compounds are bactericidal against *E. coli, Staphylococcus aureus, Streptococcus pneumoniae, Bacillus subtilis, Bacillus pumilus, Bacillus cereus, Acinetobacter baumanii, Helicobacter pylori, M. smegmatis*, NTM such as *Mycobacterium avium* and *Mycobacterium abscessus* or *M. tuberculosis*, preferably, *M. tuberculosis*.

In another embodiment, the compounds are bactericidal against drug resistant bacterial pathogens, preferably, *M. tuberculosis* and *Staphylococcus aureus*. In another embodiment, the compounds have activity against drug resistant biofilms formed by bacterial pathogens such as NTM.

In one embodiment, the compounds are used as antibacterial drugs in general or pathogen specific therapy. The compounds according to the current invention can be used in treatment of infectious diseases, preferably, Tuberculosis. In some embodiments, the compounds can be used in combination with other drugs for infectious diseases to achieve synergistic effects for overcoming the resistance problem and reducing time required for treatment. Preferably, the infectious disease is Tuberculosis.

In one embodiment, the molecular scaffold can lead to compounds that represent a new class of bactericidal antimycobacteria agents with topoisomerase I being involved in the cellular mode of action.

In one embodiment, the present invention provides compounds and salts and derivatives thereof. Derivatives of the compounds include any pharmaceutically acceptable ester, salt of an ester, alcohol, diol, ether, aldehyde, ketone, carboxylic acid or enol of a compound that can be made from the compounds by a chemical or physical process. The compounds may be in a purified form.

In one embodiment, the current invention provides a pharmaceutical composition comprising one or more of the compounds. The composition further comprises a pharmaceutically acceptable carrier and/or diluent allowing the transport of the complexes to the target within the animal after administration. The carrier and/or diluent can generally be any suitable medium by which the desired purpose is achieved and that does not affect the conjugates' capability to be directed to the desired target and to transport the active agent to this target for the desired effect. Particularly, the carrier and/or diluent should not deteriorate the pharmacological potency of the active agent and the capability of the complex to be directed to a desired target within, or on, the animal body. Preferably, said carrier and/or diluent is/are selected from water, physiologically acceptable aqueous solutions containing salts and/or buffers and any other solution acceptable for administration to an animal. Such carriers and diluents are well known to a person skilled in this field and can be, for example, distilled water, de-ionized water, pure or ultrapure water, saline, phosphate-buffered saline (PBS), solutions containing usual buffers which are compatible with the other components of the drug targeting system etc.

In certain embodiments, the pharmaceutical compositions can also include additional pharmaceutical active compounds know in the art. One or more additional antibiotics may also be included in the composition. These antibiotics may be, but not limited to, beta-lactams, macrolides, tetracyclines, quinolones, aminoglycosides, sulfonamides, glycopeptides, and oxazolidines. Moreover, the composition may be in a sterile form.

In a further embodiment, the compounds are in a pharmaceutically acceptable salt form or a form of free base. Examples of pharmaceutically acceptable salts include, without limitation, the nontoxic inorganic and organic acid addition salts such as the acetate, aconate, ascorbate, benzenesulfonate, benzoate, cinnamate, citrate, embonate, enantate, formate, fumarate, glutamate, glycolate, hydrochloride, hydrobromide, lactate, maleate, alonate, mandelate, methanesulfonate, naphthalene-2-sulphonate, nitrate, perchlorate, phosphate, phthalate, salicylate, sorbate, stearate, succinate, sulphate, tartrate, toluene-p-sulphonate, and the like.

In one embodiment, the composition may further contain pharmaceutically acceptable ingredients including metal salts and buffers. Metal salts of the compounds include alkali metal salts, such as the sodium salt of a compound containing a carboxyl group. The composition may also contain other acids such as oxalic acid, which may not be considered pharmaceutically acceptable, but may be useful in the preparation of salts.

In one embodiment, the compounds may be provided in un-solvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to un-solvated forms. In addition, the compounds, their salts, and derivatives may be hydrated or anhydrous.

In one embodiment, the pharmaceutical composition comprising compounds according to the invention, together with a conventional adjuvant, carrier, or diluent, may thus be placed into the form of solids including tablets, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds.

In a further embodiment, the composition is in the powder form. The pharmaceutically accepted carrier is a finely divided solid which is in a mixture with the finely divided active compounds. In another embodiment, the composition is in the tablet form. The active component is mixed with the pharmaceutically accepted carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In a further embodiment, the composition is in other solid forms including capsules, pills, cachets, and lozenges which are suitable for oral administration.

In one embodiment, the current invention provides a pharmaceutical composition for treating conditions involving bacterial infection, preferably Tuberculosis.

In one embodiment, the current invention also provides methods for treating a bacterial infection in a subject, comprising administering, to a subject in need of such treatment, an effective amount of the pharmaceutical composition comprising a compound according to the subject invention. The subjects may refer to any animal including, but not limited to, humans, non-human primates, rodents, and the like. In a preferred embodiment, the subject is a human. In another preferred embodiment, the human is infected with mycobacteria, in particular, *M. tuberculosis*.

In one embodiment, the current invention provides methods for treating a patient with Tuberculosis, comprising the administration of the pharmaceutical composition. The composition described herein has effective antibacterial activity and are selective for bacterial topoisomerase I inhibition. In a further embodiment, the composition targets and inhibits MtbTopI.

In one embodiment, the current invention provides methods for inhibiting a topoisomerase in a subject, comprising administering, to a subject in need of such inhibition, an effective amount of the pharmaceutical composition comprising a compound according to the subject invention. In a further embodiment, the topoisomerase is a bacterial topoisomerase, such as *M. tuberculosis* topoisomerase I. In another embodiment, the subject is a human or a bacterium. In a preferred embodiment, the bacterium is *M. tuberculosis*.

In specific embodiments, the compounds may be administered in the range of from 0.01 mg/kg body weight to 1 g/kg body weight, preferably, 1 mg·kg to 500 mg/kg body weight, more preferably, 50 mg/kg to 500 mg/kg body weight.

In one embodiment, the effective amount of said pharmaceutical composition can be administered through oral, rectal, bronchial, nasal, topical, buccal, sub-lingual, transdermal, vaginal, intramuscular, intraperitoneal, intravenous, intra-arterial, intracerebral, interaocular administration or in a form suitable for administration by inhalation or insufflation, including powders and liquid aerosol administration, or by sustained release systems such as semipermeable matrices of solid hydrophobic polymers containing the compound(s) of the invention. Administration may be also by way of other carriers or vehicles such as patches, micelles, liposomes, vesicles, implants (e.g. microimplants), synthetic polymers, microspheres, nanoparticles, and the like.

In one embodiment, the composition may be formulated for parenteral administration (e.g. by injection, for example bolus injection or continuous infusion). In addition, the composition may be presented in unit dose form in ampoules, pre-filled syringes, and small volume infusion or in multi-dose containers with or without an added preservative. The compositions may be in forms of suspensions, solutions, or emulsions in oily or aqueous vehicles. The composition may further contain formulation agents such as suspending, stabilizing and/or dispersing agents. In a further embodiment, the active ingredient of the composition according to the invention may be in powder form, obtained by aseptic isolation of sterile solid or by lyophilization from solution for constitution with a suitable vehicle, e.g. sterile, pyrogen-free water, before use.

In one embodiment, the composition may be formulated in aqueous solutions for oral administration. The composition may be dissolved in suitable solutions with added suitable colorants, flavours, stabilising and thickening agents, artificial and natural sweeteners, and the like. In addition, the composition may further be dissolved in solution containing viscous material, such as natural or synthetic gums, resins, methylcellulose, sodium carboxymethylcellulose, or other well-known suspending agents.

In one embodiment, the composition is applied topically or systemically or via a combination of both. The composition may be formulated in the forms of lotion, cream, gel and the like.

In one embodiment, the composition can be applied directly to the nasal cavity by conventional means, for example with a dropper, pipette or spray. The compositions may be provided in single or multi-dose form. Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin.

Furthermore, the composition may be provided in the form of a dry powder, for example a powder mix of the compound in a suitable powder base such as lactose, starch, starch derivatives such as hydroxypropylmethyl cellulose and polyvinylpyrrolidone (PVP). Conveniently, the powder carrier will form a gel in the nasal cavity. The powder composition may be presented in unit dose form for example in capsules or cartridges of, e.g., gelatin, or blister packs from which the powder may be administered by means of an inhaler.

In one embodiment, the pharmaceutical composition is provided in unit dosage forms, wherein the composition in desired form is divided into unit doses containing appropriate quantities of the active component. The unit dosage form can be a packaged preparation, the package containing discrete quantities such as packaged tablets, capsules, and powders in vials or ampoules. Moreover, the unit dosage form can be a capsule, tablet, cachet, or lozenge itself, or it can be the appropriate number of any of these in packaged form. In a preferred embodiment, tablet or capsule forms are for oral administration and liquid form are for intravenous administration and continuous infusion.

Furthermore, it would be understood by those skilled in the art that the methods described in the present invention would not only apply to treatment in a subject, but could be applied to cell cultures, organs, tissues, or individual cells in vivo or in vitro, including tumors, and immortalized cells isolated or derived from a subject.

The present invention also provides methods of inhibiting topoisomerase in bacteria, comprising the administration of an effective amount of one or more of the compounds and/or the pharmaceutical compositions as described herein to one or more bacteria. In one embodiment, the topoisomerase is the type IA topoisomerase, preferably, bacterial topoisomerase I, more preferably, EcTopI and MtbTopI.

The present invention also provides kits comprising the compounds and/or pharmaceutical compositions as described herein. The kits may further be used in the methods described herein. The kits may also include at least one reagent and/or instruction for their use. Moreover, the kits may include one or more containers filled with one or more compounds and/or pharmaceutical composition described in the present invention. The kits may also comprise a control composition, such as a control antibiotic.

EXAMPLES

The invention is further described by reference to the following examples which are intended to illustrate, not to limit the scope of the invention.

Example 1

Synthesis of Library 2229 and Individual Compounds and Construction of Scaffold Ranking Plate Scaffold Ranking Library The scaffold ranking library contains one sample for each of the 50 positional scanning libraries tested. Each of these samples contains an approximate equal molar amount of each compound in that library. The sample 2229 in the scaffold ranking library contains 345,600 compounds in approximately equal molar amounts. These scaffold ranking library samples can be prepared by mixing the cleaved products of the complete positional scanning library, or they can be synthesized directly as a single mixture, as was the case with 2229 (29, 30-32).

Positional Scanning Libraries 2229, 2471 and 2580.

The polyamine positional scanning libraries 2229, 2471, 2580 and all polyamine individual compounds were synthesized using the scheme described below:

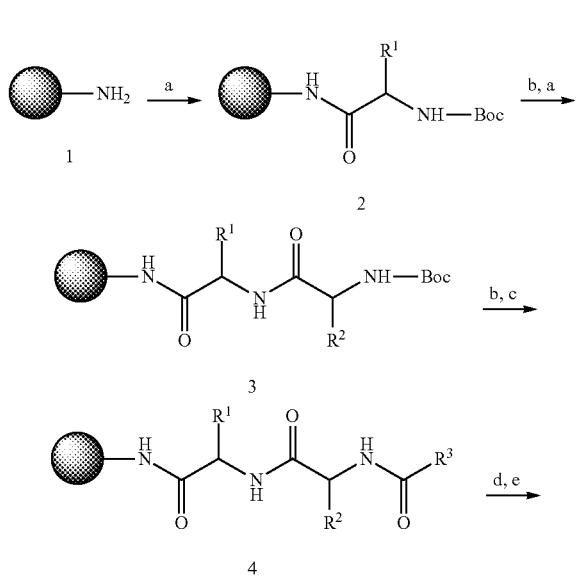

-continued

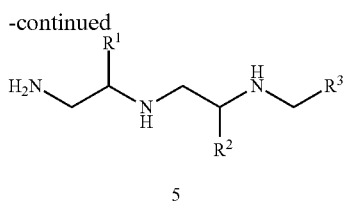

wherein a, amino acid coupling; b, Boc deprotection; c, carboxylic acid coupling; d, exhaustive reduction; e, cleavage from resin.

The positional scanning library 2229 contains 284 samples and incorporates both individual and mixtures of amino acids ($R^1$ and $R^2$) and carboxylic acid ($R^3$). The synthetic technique facilitates the generation of information regarding the likely activity of individual compounds from the screening of the library (29, 33, 34). Equimolar isokinetic ratios have been previously determined and calculated for each of the amino and carboxylic acids utilized for the respective mixtures (35, 36). The polyamine library 2229 has a total diversity of 345,600 compounds (60×60×96=345,600). The $R^1$ and $R^2$ position were derived from 60 amino acids and the $R^3$ position was derived from 96 carboxylic acids.

Libraries 2229, 2471, and 2580 as well as the individual compounds reported herein (Compounds XXX) were synthesized following the same synthetic scheme as shown above (37, 38). Utilizing the "tea-bag" methodology (39), 100 mg of p-methylbenzhydrylamine (MBHA) resin (1.1 mmol/g, 100-200 mesh) was sealed in a mesh "tea-bag", neutralized with 5% diisopropylethylamine (DIEA) in dichloromethane (DCM) and subsequently swelled with additional DCM washes. Boc-Amino Acids (R1) were coupled in Dimethylformamide (0.1M DMF) for 120 mins in the presence of Diisopropylcarbodiimide (DIC, 6 equiv.) and 1-Hydroxybenzotriazole hydrate (HOBt, 6 equiv.) (Step 1). The Boc protecting group was then removed with Trifluoroacetic Acid (TFA) in DCM for 30 mins and subsequently neutralized with 5% DIEA/DCM (3×). Boc-Amino Acids (R2) were coupled utilizing standard coupling procedures (6 equiv.) with DIC (6 equiv.) and HOBt (6 equiv.) in DMF (0.1 M) for 120 mins. The Boc group was removed with 55% TFA/DCM for 30 mins and subsequently neutralized with 5% DIEA/DCM (3×). Carboxylic acids (R3) were coupled using (10 equiv.) in the presence of DIC (10 equiv.) and HOBt (10 equiv.) in DMF (0.1 M) for 120 mins (Step 3). All coupling reactions were monitored for completion using Ninhydrin. The reduction was performed in a 4000 mL Wilmad LabGlass vessel under nitrogen. 1.0 M Tetrahydrofuran (THF) borane complex solution was used in 40-fold excess for each amide bond. The vessel was heated to 65° C. and maintained at this temperature for 96 hrs. The solution was then removed and the bags were washed with THF and methanol (MeOH). Once completely dry, the bags were treated overnight with piperidine at 65° C. and washed several times with DMF, DCM and methanol. As previously reported by our group and others, the reduction of polyamides with borane is free of racemization (40-42). Completion of reduction was monitored by LCMS analysis of a control compound that was cleaved from the solid support (HF, anisole, 0° C. 7 hr). The resin was cleaved with HF in the presence of anisole in an ice bath at 0° C. for 7 hours. After removal of the HF by gaseous N2, the products were then extracted from the vessels with 95% acetic acid in water, transferred to scintillation vials, frozen and lyophilized. The compounds were then reconstituted in 50% acetonitrile and water, frozen and lyophilized three more times. For initial screening the individual compounds were tested as crude material in case the activity is driven by some side reaction that was also present in the original positional scanning library. After this initial screening, compounds 2471-12, 2471-24 and 2471-80 were selected for purification and NMR characterization.

LCMS Analysis

The purity and identity of all compounds was verified using a Shimadzu 2010 LCMS system, consisting of a LC-20AD binary solvent pump, a DGU-20A degasser unit, a CTO-20A column oven, and a SIL-20A HT autosampler. A Shimadzu SPD-M20A diode array detector was used for detection. A full spectra range of 190-600 nm was obtained during analysis. Chromatographic separations were obtained using a Phenomenex Luna C18 analytical column (5 µm, 50×4.6 mm i.d.) preceded by a Phenomenex C18 column guard (5 µm, 4×3.0 mm i.d.). All equipment was controlled and integrated by Shimadzu LCMS solutions software version 3 Mobile phases for LCMS analysis were HPLC grade or LCMS grade obtained from Sigma Aldrich and Fisher Scientific. The mobile phases consisted of a mixture LCMS grade Acetonitrile/water (both with 0.1% formic acid for a pH of 2.7). The initial setting for analysis was set at 5% Acetonitrile (v/v), then was linearly increased to 95% Acetonitrile over 6 mins. The gradient was then held at 95% Acetonitrile for 2 mins, linearly decreased to 5% over 0.10 mins and held for an additional 1.90 mins. The total run time was equal to 12 mins. The total flow rate was set to 0.5 mL/minute. The column oven and flow cell temperature for the diode array detector was set at 30° C. The autosampler temperature was held at 15° C. 5 µl of compound was injected for analysis.

HPLC Purification and NMR (Compounds 2471-12, 2471-24, 2471-80)

All purifications were performed on a Shimadzu Prominence preparative HPLC system, consisting of LC-8A binary solvent pump, a SCL-10A system controller, a SIL-10AP autosampler, and a FRC-10A fraction collector. A Shimadzu SPD-20A UV detector was used for detection. The wavelength was set at 214 nm during analysis. Chromatographic separations were obtained using a Phenomenex Luna C18 preparative column (5 µm, 150×21.5 mm i.d.) preceded by a Phenomenex C18 column guard (5 µm, 15×21.2 mm i.d.). Prominence prep software was used to set all detection and collection parameters. The mobile phases for HPLC purification were HPLC grade obtained from Sigma Aldrich and Fisher Scientific. The mobile phase consisted of a mixture of Acetonitrile/water (both with 0.1% formic acid). The initial setting for separation was set at 2% (v/v) Acetonitrile, which was held for 2 mins and the gradient was linearly increased to 20% (v/v) Acetonitrile over 4 mins. The gradient was then linearly increased to 55% (v/v) Acetonitrile over 36 mins. The HPLC system was set to automatically flush and re-equilibrate the column after each run for a total of 4 column volumes. The total flow rate was set to 12 mL/min and the total injection volume was set to 3900 µl. The fraction collector was set to collect from 6 to 40 mins. The corresponding fractions were then combined and lyophilized. The 1H spectra were obtained utilizing the Bruker 400 Ascend (400 MHz). NMR chemical shifts were reported in δ (ppm) using the δ 7.26 signal of CDCl3 (1H NMR).

Chemical Synthesis of Individual Compounds (S)—N6-methyl-N2-((S)-2-(naphthalen-1-ylmethyl-amino)hexyl)hexane-1,2,6-triamine (2471-12)

Using the synthetic approach described above, 2471-12 was synthesized using the following reagents: Boc-L-Lysine (ClZ) (R1), Boc-L-Norleucine (R2), 1-naphthoic acid (R3). Final crude product was purified by HPLC as described above. 1H NMR (400 MHz, CHLOROFORM-d): δ 8.15 (br. s., 4 H) 8.01 (s, 1 H) 7.97 (s, 1 H) 7.85 (br. s., 7 H) 7.60 (br. s., 4 H) 7.51 (br. s., 5 H) 6.01 (br. s., 8 H) 4.71 (br. s., 4 H) 3.28 (br. s., 2 H) 3.18 (br. s., 2 H) 3.09 (br. s., 3 H) 3.00 (br. s., 5 H) 2.89 (br. s., 5 H) 2.81 (br. s., 4 H) 2.60 (br. s., 5 H) 2.03 (br. s., 1 H) 1.70 (br. s., 7 H) 1.60 (br. s., 3 H) 1.51 (br. s., 3 H) 1.38 (br. s., 7 H) 1.16 (br. s., 8 H) 1.00 (br. s., 4 H) 0.65-0.91 (m, 9 H). LCMS (ESI+) C24H40N4 m/z 385.33 found [M+H]+:385.20.

(S)—N2-((S)-2-(naphthalen-1-ylmethylamino)hexyl) butane-1,2,4-triamine (2471-24)

Using the synthetic approach described above, 2471-24 was synthesized using the following reagents: Boc-L-Asparagine(Xan) (R1), Boc-L-Norleucine (R2), 1-Naphthoic acid (R3). Final crude product was purified by HPLC as described above. 1H NMR (400 MHz, CHLOROFORM-d): δ8.30 (br. s., 6 H) 8.03 (br. s., 8 H) 7.74 (br. s., 13 H) 7.50 (br. s., 7 H) 7.40 (br. s., 7 H) 7.14 (br. s., 2 H) 7.06 (br. s., 2 H) 6.98 (br. s., 5 H) 6.41 (br. s., 2 H) 4.57 (br. s., 3 H) 2.95 (br. s., 11 H) 2.02 (br. s., 1 H) 1.90 (br. s., 1 H) 1.81 (br. s., 2 H) 1.52 (br. s., 5 H) 1.25 (d, J=7.58 Hz, 2 H) 1.11 (br. s., 3 H) 1.01 (br. s., 5 H) 0.89 (br. s., 4 H) 0.64 (br. s., 10 H) 0.41 (br. s., 2 H). LCMS (ESI+) calculated for C21H34N4 m/z 343.28 found [M+H]+:354.15.

(S)—N1-((S)-1-amino-3-(naphthalen-1-yl)propan-2-yl)-N5-methyl-N2-(2-(naphthalen-2-yl)ethyl)pentane-1,2,5-triamine (2471-80)

Using the synthetic approach described above, 2471-80 was synthesized using the following reagents: Boc-3-(2-naphthyl)-L-alanine (R1), Boc-L-Ornithine(Z) (R2), 1-Naphthaleneacetic acid (R3). Final crude product was purified by HPLC as described above. 1H NMR (400 MHz, CHLOROFORM-d): δ8.24 (br. s., 1 H) 8.13 (br. s., 1 H) 7.95 (d, J=18.58 Hz, 1 H) 7.70-7.86 (m, 3 H) 7.68 (br. s., 2 H) 7.61 (br. s., 1 H) 7.45 (s, 2 H) 7.41 (s, 2 H) 7.34 (br. s., 1 H) 7.28 (br. s., 2 H) 3.61 (br. s., 2 H) 3.42 (br. s., 1 H) 3.34 (br. s., 2 H) 3.16 (br. s., 2 H) 2.87-3.08 (m, 5 H) 2.73-2.87 (m, 2 H) 2.60 (br. s., 1 H) 1.48 (br. s., 1 H). LCMS (ESI+) calculated for C31H40N4 m/z 469.33 found [M+H]+: 469.15.

Example 2

Antibacteral Activity of the Compounds

Bacterial Strains and Plasmids

Bacterial strains and plasmids used this study are listed in Table 2. Mtb topA gene encoding topoisomerase I (MtbTopI) was PCR amplified using primers containing BamH1 and Sca1 restriction sites and cloned into the TA cloning vector (pCR2.1-TOPO from Invitrogen) resulting in pTAmtop. Plasmid pKW08-Lx (gift of Brian Robertson, Addgene) is an E. coli-mycobacteria shuttle vector containing the luxAB genes under the control of a tetracycline inducible promoter TetRO (43). The BamH1-Sca1 fragment of pKW08-Lx containing luxAB genes was replaced by the BamH1-Sca1 fragment from pTAmtop containing Mtb topA gene. The resulting plasmid, pTA-M+, expressed tetracycline inducible MtbTopI. A control plasmid, pKW-nol was also constructed when pKW08-Lx was religated following the removal of the luxAB genes. These plasmids were electroporated into M. smegmatis mc2 155 separately and the resulting strains were used in growth inhibition assays.

TABLE 2

Strains and Plasmids

| | Genotype or Description | Source |
|---|---|---|
| Strain | | |
| M. smegmatis mc2 155 | | ATCC |
| M. tuberculosis CDC1551 | pMV306hsp + LuxG13 | gift from Brian Robertson and Siouxsie Wiles (Addgene plasmid #26161) (44) |
| Plasmid | | |
| pKW08-Lx | Tetracycline inducible expression plasmid | gift from Brian Robertson (Addgene plasmid # 25012) (43) |
| pTAmtop | PCR clone of topA gene coding for MtbTopI | This work |
| pTA-M+ | Luciferase gene in pKW08-Lx replaced by M. tuberculosis topA | This work |
| pTA-nol | PKW08 derived clone with no insert | This work |

For analysis of compound activity against Mtb, Mtb CDC1551 constitutively expressing the luxCDABE operon from an integrated pMV306hsp+LuxG13 plasmid (Mtb::lux) was cultured in Middlebrook 7H9 broth containing 0.5% glycerol, 0.05% Tween 80 and OADC supplement (oleic acid, albumin, dextrose, catalase) or 7H10 agar media supplemented with OADC. Kanamycin (50 μg/mL) was added to broth cultures for selection where appropriate. pMV306hsp+LuxG13 was a gift from Brian Robertson and Siouxsie Wiles (Addgene plasmid #26161) (44).

Bacterial Topoisomerase I Relaxation Activity Inhibition Assay

The relaxation activity of bacterial topoisomerase I was assayed in a buffer containing 10 mM Tris-HCl, pH 8.0, 50 mM NaCl, 0.1 mg/mL gelatin, and 0.5 mM MgCl$_2$. One microliter of the compounds dissolved in DMF (dimethylformamide) or solvent alone was mixed with 10 μl of the reaction buffer containing 10 ng of enzyme before the addition of 9 μl of reaction buffer containing 160 ng of supercoiled pBAD/Thio plasmid DNA purified by cesium chloride gradient as substrate. Following incubation at 37° C. for 30 min, the reactions were terminated by the addition of 4 μl of 50% glycerol, 50 mM EDTA, and 0.5% (v/v) bromophenol blue, and analyzed by agarose gel electrophoresis. The gels were stained in ethidium bromide and photographed under UV light.

DNA Gyrase Supercoiling Inhibition Assay

DNA gyrase (obtained from New England BioLabs) supercoiling assays were carried out by mixing the compounds with 2 U of the enzyme in reaction buffer supplied by the manufacturer, followed by the addition of 300 ng of relaxed covalently closed circular DNA was for a final reaction volume of 20 μL. The samples were incubated at 37° C. for 30 minutes before being terminated by the addition of a buffer containing 5% SDS, 0.25% bromophenol blue, and 25% glycerol. The reactions were then analyzed by agarose gel electrophoresis.

Figure 1B:
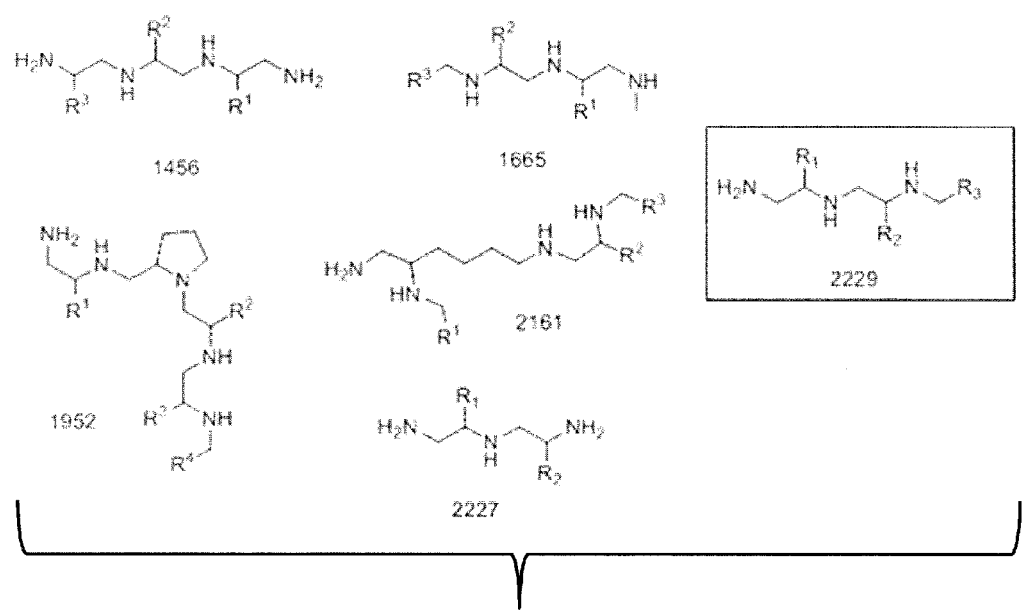

Selection of Polyamine Scaffold as Platform for Inhibitors of Bacterial Topoisomerase I from Screening of Scaffold Ranking Library Mixtures In order to identify novel inhibitors of bacterial topoisomerase I, fifty scaffold ranking library mixtures were assayed at 100 μg/ml for inhibition of the relaxation activity of EcTopI. Scaffold ranking library 2229 was the only library mixture that showed >50% inhibition of the EcTopI relaxation activity (FIG. 1A). This is not due to non-specific inhibition of the topoisomerase activity by the positively charged polyamine structure, as the supercoiling activity of type IIA topoisomerase DNA gyrase was not inhibited by library 2229 compounds at similar concentrations (FIG. 1A). There are five other polyamine scaffolds (FIG. 1B) among the 50 scaffold ranking mixtures tested in this study, and only library 2229 was found to inhibit EcTopI relaxation activity at 100 μg/mL.

Individual Small Molecule Inhibitors of Bacterial Topoisomerase I

The 284 samples in the positional scanning library 2229 were each assayed for inhibition of the relaxation activity of EcTopI. The effects of different $R^1$, $R^2$, $R^3$ substitutions in the positional scanning library on the $IC_{50}$ values for inhibition of EcTopI relaxation activity were analyzed. Several structure activity relationship (SAR) trends are apparent within the positional scanning data. At the $R^1$ position, there is a preference for positively charged functional groups or large aromatics which produce $IC_{50}$ values for inhibition of the relaxation activity of EcTopI in the low μM range. Simple aliphatic substitutions at $R^1$ produce compounds with $IC_{50}$ values greater than 100 μM. The positional scanning data was used to direct the synthesis of individual compounds. In cases where SAR trends were observed (as for $R^1$ described above), substitutions were selected to prepare those compounds most likely to be active. In the other instances, individual substitutions were selected to generate diversity around the scaffold. This information was utilized for the design of the 2471 series of 80 individual compounds. The $IC_{50}$ concentrations for inhibition of 50% of the relaxation activity of EcTopI for these 80 individual compounds were found to range from 1.25 μM to >160 μM (Table 1). While the eighteen individual 2471 series compounds with $IC_{50}$ values at 20 μM or less for inhibition of EcTopI relaxation activity all contain a naphthyl group at the $R^3$ position (Table 1), a number of additional compounds were made with alternative substitutions at $R^3$ (i.e. dihydroxyphenyl, halogenated phenyls, aliphatic groups, etc.); however, all of these additional compounds exhibit $IC_{50}$ values greater than 20 μM for inhibition of EcTopI relaxation activity (Table 1), indicating the importance of the naphthyl group in this position.

Example 3

Figure 2:
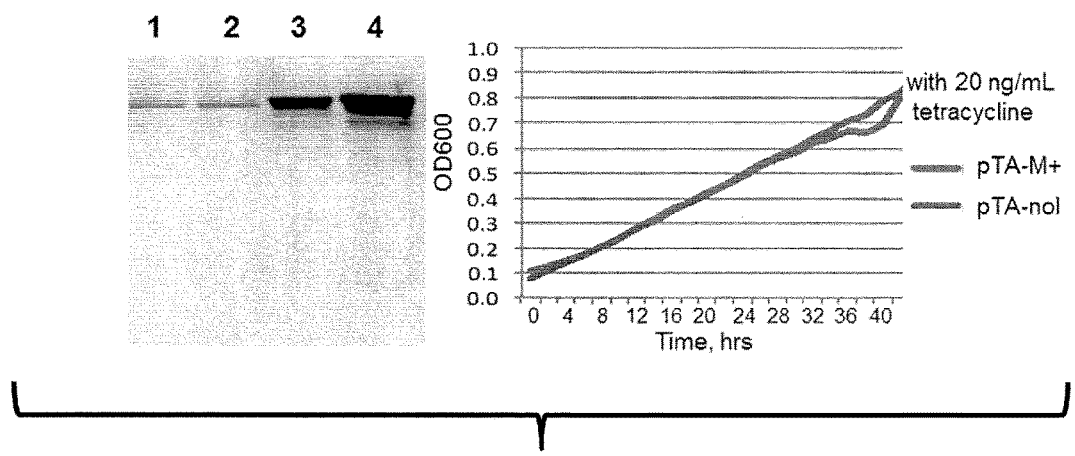
FIG. 2. Overexpression of recombinant MtbTopI in *M. smegmatis*. Left: Western blot analysis of mycobacteria topoisomerase I levels. The whole cell lysates of *M. smegmatis* transformed with pTA-nol (lanes 1,2) or pTA-M+ (lanes 3,4) cultured with no inducer added (lanes 1,3) or induced with 20 ng/mL tetracycline (lanes 2, 4) were analyzed by western blot using rabbit polyclonal antibodies against MtbTopI. Right: Growth of induced cultures monitored by Absorbance at 600 nm.

Inhibitors with Anti-Mycobacterial Activity Sensitive to Overexpression of Topoisomerase I A subset of these eighteen compounds from library 2471 was able to inhibit the growth of *M. tuberculosis* (Table 3). The cytotoxicity of these compounds against mammalian cells is also shown in Table 3. Inhibition of MtbTopI relaxation activity was similar to inhibition of EcTopI. Transformants of *M. smegmatis* overexpressing recombinant MtbTopI or with cloning vector only were used to investigate if topoisomerase I activity is involved in the antimycobacterial mode of action. Overexpression of recombinant MtbTopI was achieved by replacing the luciferase gene in pKW08-Lx plasmid with the MtbTopI gene. In the absence of tetracycline inducer, the level of topoisomerase I in *M. smegmatis* transformed by pTA-M+ was found by western blot and densitometry analysis to be 6-fold higher than the topoisomerase I level in *M. smegmatis* transformed with control plasmid pTA-nol (FIG. 2). Addition of 20 ng/mL tetracycline can further increase the overexpression to ~9-fold, but there was also an observable effect of growth inhibition from MtbTopI overexpression induced by tetracycline (FIG. 2). Therefore the effect of MtbTopI overexpression on sensitivity to topoisomerase I inhibitors was tested in cultures grown in the absence of tetracycline.

TABLE 3

Antimycobacterial activity and cytotoxicity of the most potent bacterial topoisomerase I inhibitors characterized in this study ($IC_{50}$ ≤ 20 μM)

| Compound | EcTopI $IC_{50}$, μM | MtbTopI $IC_{50}$, μM | MIC, μM *M. smegmatis* mc2 155 | Percent Mtb-lux killing 5 μg/mL | Percent HEK toxicity 6.25 μg/mL |
|---|---|---|---|---|---|
| 2471-18 | 1.25 | 1.25 | 50 | 22.7 | 16.3 |
| 2471-27 | 1.25 | 1.9 | 25 | 12.6 | 5.2 |
| 2471-15 | 1.9 | 0.625 | 50 | 5.4 | 17.0 |
| 2471-3 | 2.5 | 2.5 | 50 | 5.9 | 20.9 |
| 2471-6 | 2.5 | 1.25 | 25 | 30.7 | 10.0 |
| 2471-30 | 2.5 | 2.5 | 25 | 35.8 | 18.7 |
| 2471-80 | 2.5 | 5 | 12.5 | 91.6 | 33.2 |
| 2471-9 | 5 | 5 | 50 | 58.6 | 16.6 |
| 2471-33 | 5 | 5 | 50 | 56.0 | 11.7 |
| 2471-12 | 7.5 | 7.5 | 25 | 70.9 | 15.2 |
| 2471-21 | 7.5 | 10 | 50 | 42.0 | 8.2 |
| 2471-24 | 10 | 7.5 | 50 | 64.3 | 5.4 |
| 2471-36 | 20 | 15 | 25 | 99.2 | 15.3 |
| 2471-76 | 20 | 10 | 12.5 | 60.7 | 18.4 |

Growth inhibition assays showed that the MIC values against *M. smegmatis* for four of the compounds, 2471-12, 2471-24, 2471-36 and 2471-80 were increased by 2-4 fold with overexpression of recombinant MtbTopI (Table 4). The overexpression of MtbTopI has no effect on the MIC of ciprofloxacin, so topoisomerase I overexpression did not have a general non-specific effect on sensitivity to antibacterial compounds. Determination of viable colony counts demonstrated that these compounds are bactericidal against

Figure 3:
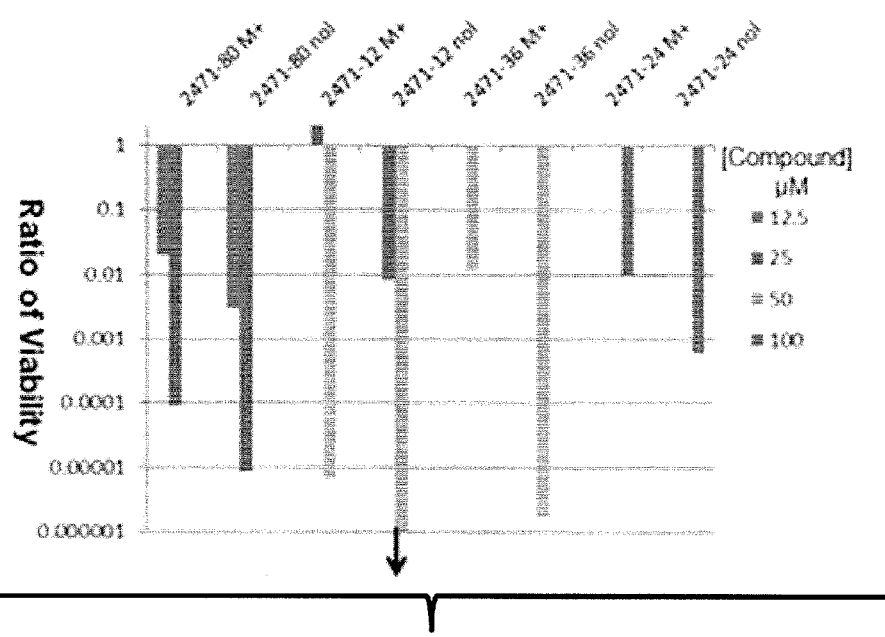
FIG. 3. Effect of MtbTopI overexpression on the bactericidal effect of selected topoisomerase I inhibitors. The MBC90 values against *M. smegmatis* mc2 155 is shown in the table. The loss of viability following treatment with compounds for 44 hr was compared between transformants overexpressing MtbTopI (M+) from pTA-M+ and with control vector pTA-nol(nol).
Figure 4:
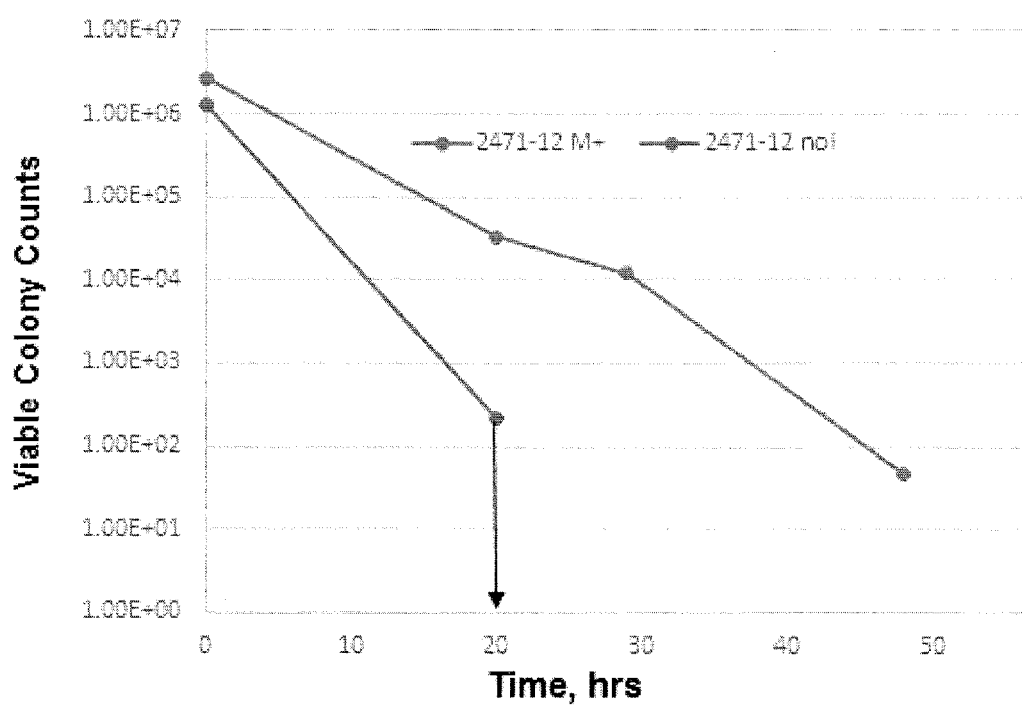
FIG. 4. Effect on MtbTopI overexpression on time course of *M. smegmatis* cell killing by inhibitor 2471-12. Viable colony counts of *M. smegmatis* transformed with either pTA-M+ (M+) or pTA-nol(nol) were determined prior to and following treatment with 50 μM of compound 2471-12.
Figure 5A:
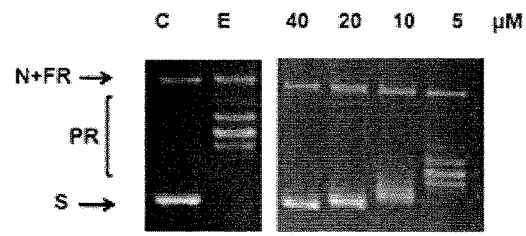
FIGS. 5A-5D. Assay of topoisomerase activity inhibition by 2471-80. C: DNA substrate only; E: enzyme with DMF control. S: supercoiled plasmid DNA; N: nicked DNA; FR: fully relaxed DNA; PR: partially relaxed DNA; (5A) *M. tuberculosis* topoisomerase I relaxation activity assay. (5B) *E. coli* DNA gyrase supercoiling activity assay. CIP: 150 μM ciprofloxacin. (5C) human topoisomerase I relaxation activity assay. CPT: 100 μM camptothecin. (5D) human topoisomerase IIα decatenationassay. mAMSA: 75 μM mAMSA. The gel panels shown for each assay are images from the same gel.
Figure 5B:
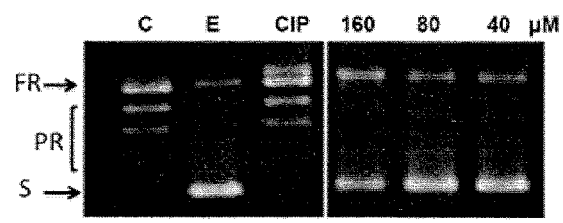
Figure 5C:
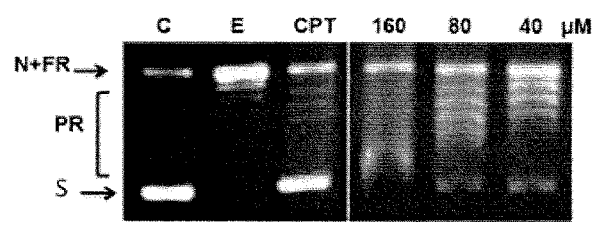
Figure 5D:
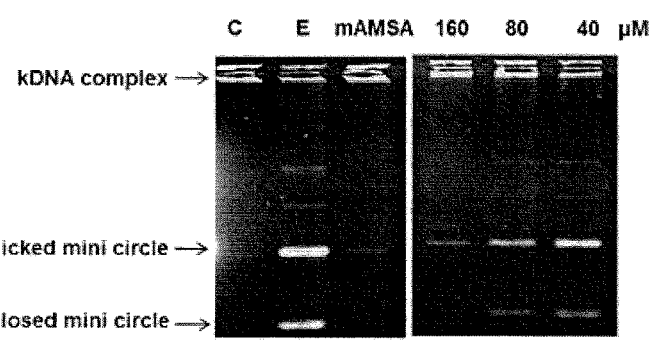

*M. smegmatis*, and loss of viability after treatment with the compounds for 44 hours was also less severe when recombinant MtbTopI is overexpressed (FIG. 3). The time course of loss of viable colony counts following treatment with 50 µM of compound 2471-12 (FIG. 4) showed clearly the rapid killing of *M. smegmatis* transformed with control cloning vector, and the reduction of cell killing by this inhibitor with MtbTopI overexpression.

TABLE 4

Effect of recombinant MtbTop1 overexpression on MICs (µM) of select compounds against *M. smegmatis* mc2 155

| Compound | Structure | MIC, *M. smegmatis* mc2 155/pTA-noI | MIC, *M. smegmatis* mc2 155/pTA-M+ |
|---|---|---|---|
| 2471-12 | 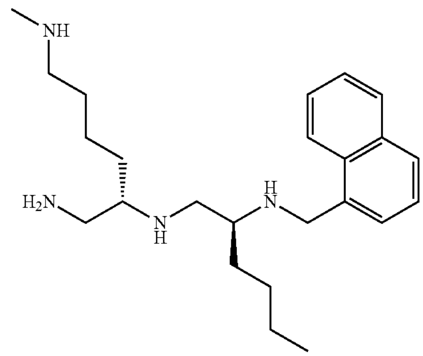 [SMILES: CCCC[C@@H](CN[C@H](CN)CCCCNC)NCc1cccc2ccccc12] | 12.5 | 50 |
| 2471-24 | 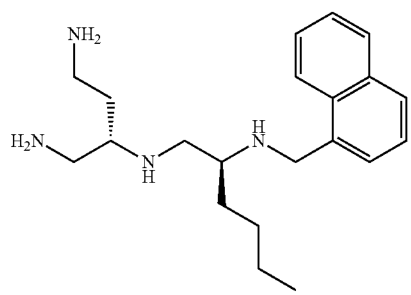 [SMILES: CCCC[C@@H](CN[C@H](CN)CCN)NCc1cccc2ccccc12] | 25 | 50 |
| 2471-36 | 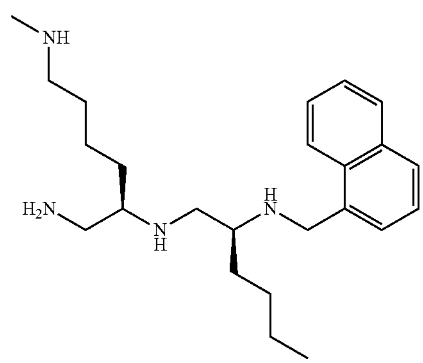 [SMILES: CCCC[C@@H](CN[C@@H](CN)CCCCNC)NCc1cccc2ccccc12] | 25 | 50 |
| 2471-80 | 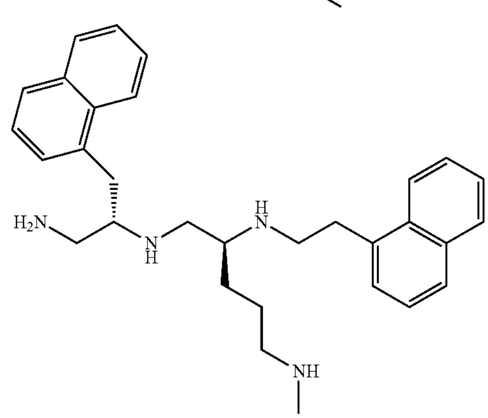 | 6.25 | 12.5 |

Example 4

Bactericidal Activity of the Compounds

Assay of *M. smegmatis* Growth Inhibition and Loss of Viability

Cells were cultured from individual colonies in Middlebrook 7H9 medium supplemented with 0.2% glycerol, 0.05% Tween 80, and 10% albumin, dextrose, sodium chloride for one day. For the strains with plasmids, 50 µg/mL hygromycin B was included. The culture was then diluted 1:500 with the same medium without ADN and grown until OD600 was between 0.6 and 0.7. After adjustment of OD600 to 0.5, the cultures were diluted 1:10, and 50 µL were added to clear round bottom 96-well plates containing 50 µL of the same medium with compounds added. The plates were then incubated with shaking at 37° C. for 48 hours, with absorbance readings being taken at approximately every 4 hours. The minimum inhibitory concentration was determined to be the minimum compound concentration that prevented increase in absorbance over time.

Assay of *M. tuberculosis* Growth Inhibition by Bioluminescence and CFU Assays

Stock solutions of compounds 2471-12, 2471-24, 2471-36 and 2471-80 at 25 mM in 100% DMSO were diluted in water to obtain a 5× working stock (500 µM in 2% DMSO). Twelve-point 2-fold serial dilutions of compounds in sterile media were done using a robotic liquid handler (Biotek Precision), with one fifth volume (6 µl) of compound per well of solid white 384-well plates. Final concentrations of compounds ranged from 100 µM to 0.02 µM, with each one tested in triplicate. Cultures of Mtb::lux at mid log phase were diluted in 7H9 OADC to a final optical density (600 nm) of 0.01 before adding 24 µl/well to plates containing compounds. After 5 days incubation at 37 C, luminescence was measured using a Synergy H4 platereader (BioTek). Samples were taken from each well, serially diluted in PBS 0.05% Tween 80 and plated on 7H10. Each 384 well plate contained 8 replicate wells of the following controls which were also plated in triplicate for CFU counting: 0.4% DMSO, 10 uM, 1 uM and 0.1 uM rifampicin and isoniazid.

To determine if the compounds found to inhibit growth of the mycobacteria are bactericidal, the cells from the MIC assays treated with compound concentrations above the MIC concentrations were plated on LB agar plates after treatment with the compounds and allowed to grow at 37° C. The colonies formed were counted after 2 days. The CFU values determined were divided by the CFU of cells before treatment to determine the ratio of loss of viability.

Resazurin-Based Cytotoxicity Assay

J774 macrophages were cultured in Dulbeco's minimal essential medium (DMEM) supplemented with 10% heat inactivated fetal bovine serum. One day prior to performing the assay $2.5 \times 10^4$ cells were seeded on black 384 well. Compounds and controls (0.4% DMSO and 2% Triton X final concentrations) were added 6 hr after seeding. Survival was determined after 24 hr by resazurin reduction measurement. Addition of 0.02 mg/mL resazurin was followed by 4 hours incubation at 37° C. and subsequent fluorescence reading (530 nm/590 nm) using a Synergy H4 (BioTek) plate reader. Data are presented as a percent viability compared to the vehicle (0.4% DMSO) control with 100% being noncytotoxic.

Bactericidal Activity of 2471 Polyamine Analogs Against *M. tuberculosis*

Four compounds from library 2471 (2471-12, 2471-24, 2471-36, and 2471-80) with potent activity against purified MtbTopI and topoisomerase I-specific bactericidal activity against *M. smegmatis* were tested for antibacterial activity against Mtb using an autoluminescent strain of Mtb CDC1551 expressing an optimized bacterial luxCDABE operon (Mtb::lux). Dose-response curves revealed that all four compounds had growth inhibition $IC_{50}$ values of ~3-9 µM, a relatively potent starting point for a hit series (Table 5). Validation of these results by CFU further revealed that 2471-80 exerted particularly potent dose-dependent cidal activity, resulting in ~2-3 log greater killing than −12 or −24 at higher concentrations (3-4 log reduction vs 1 log) (data not shown). Although additional medicinal chemistry optimization is needed during hit-to-lead development, cytotoxicity concentrations ($CC_{50}$) of ~40 µM for 2471-36, 2471-80 and ~100 µM for 2471-12, 2471-24 yielded selectivity index values ($SI=CC_{50}/IC_{50}$) of >10 for three of the compounds (Table 5). Thus, 2471 compounds identified as specific inhibitors of the essential MtbTopI enzyme are able to penetrate the mycobacterial cell wall to access their intracellular target and kill Mtb.

TABLE 5

Selective antimicrobial activity against *M. tuberculosis*

| Compound | $IC_{50}$* Mtb:lux (µM) | $CC_{50}$# J774 (µM) | SI^ |
|---|---|---|---|
| 2471-12 | 6.8 | 104.3 | 15.4 |
| 2471-24 | 8.4 | 101.4 | 12 |
| 2471-36 | 3.3 | 36.49 | 11.2 |
| 2471-80 | 5.9 | 40.39 | 6.9 |

*Drug concentration leading to 50% reduction in luminescence signal compared to controls
Drug concentration leading to 50% loss of viability in J774 macrophage cell line after 24 hr exposure
^SI = $CC_{50}/IC_{50}$

Example 5

Specificity of Selected Compounds

Human Topoisomerase I Relaxation Inhibition Assay

Human topoisomerase I (obtained from TopoGen) relaxation assays were carried out with 0.5 U of enzyme in reaction buffer supplied by the manufacturer. The enzyme was mixed with the indicated concentration of compound dissolved before 160 ng of supercoiled pBAD/Thio plasmid DNA was added in the same buffer, for a final volume of 20 µL. Following incubation at 37° C. for 30 minutes, the reactions were terminated with a buffer containing 5% SDS, 0.25% bromophenol blue, and 25% glycerol, and analyzed by agarose gel electrophoresis.

Human topoisomerase IIα Decatenation Inhibition Assay

Human Topoisomerase IIα (obtained from TopoGen) assays were carried out by adding the compounds to 180 ng of kinetoplast DNA (kDNA) in the buffer supplied by the manufacturer before the addition of 2 U of the enzyme. The samples were incubated for 15 minutes at 37° C. before the addition of 4 µl of stop buffer containing 5% sarkosyl, 0.0025% bromophenol blue, and 25% glycerol. The reactions were then analyzed by electrophoresis in 1% agarose gels containing 0.5 µg ml$^{-1}$ ethidium bromide before being photographed under UV light.

Specificity of Selected Bacterial Topoisomerase I Inhibitors

Inhibition of MtbTopI relaxation activity by compounds 2471-12, 2471-24, 2471-36 2471-80, 2580-3, 2580-15, 2580-18, 2580-24, and 2580-33 was comparable to inhibition of EcTopI. Inhibition of the supercoiling of DNA gyrase, relaxation activity of human topoisomerase I, and decatenation activity of human topoisomerase IIα required >10 fold higher compound concentrations (Table 6). It is therefore unlikely that the inhibition observed for bacterial topoisomerase I is due to non-specific interaction of the positively charged compounds with DNA. In addition, FIGS. 5A-5D show the inhibition of topoisomerase by 2471-80.

TABLE 6

IC50s (μM) of Inhibition of Topoisomerase activities

| Compound | M. tuberculosis topoisomerase I | E. coli DNA gyrase | Human Topoisomerase I | Human Topoisomerase IIα |
|---|---|---|---|---|
| 2471-12 | 7.5 | 160 | 80 | 80 |
| 2471-24 | 7.5 | >160 | >160 | 160 |
| 2471-36 | 15 | >160 | >160 | >160 |
| 2471-80 | 5 | 160 | 80 | 80 |
| 2580-3 | 6 | >80 | >80 | >80 |
| 2580-15 | 0.73 | >90 | >90 | >90 |
| 2580-18 | 3.2 | >100 | >100 | >100 |
| 2580-24 | 8 | >85 | >85 | >85 |
| 2580-33 | 8 | >85 | >85 | >85 |

Example 6

Anisotropy Assay of DNA Binding by MtbTopI

Binding of MtbTopI to single-stranded DNA was assayed by change of anisotropy of a 59 base oligonucleotide modified with 6-carboxyfluorescein at the 3' end (synthesized by Biosearch Technologies) as previously described (45). All measurements were performed at room temperature in 0.5 ml of binding buffer (50 mM Tris-HCl, pH 7.5, 100 mM NaCl, 0.1 mM EDTA). Excitation and emission wavelengths were 495 and 520 nm, respectively with the excitation and emission slits set at 5 and 10 nm. Data was collected using the Advanced Reads program on a Varian Cary Eclipse fluorescence spectrophotometer.

Figure 6:
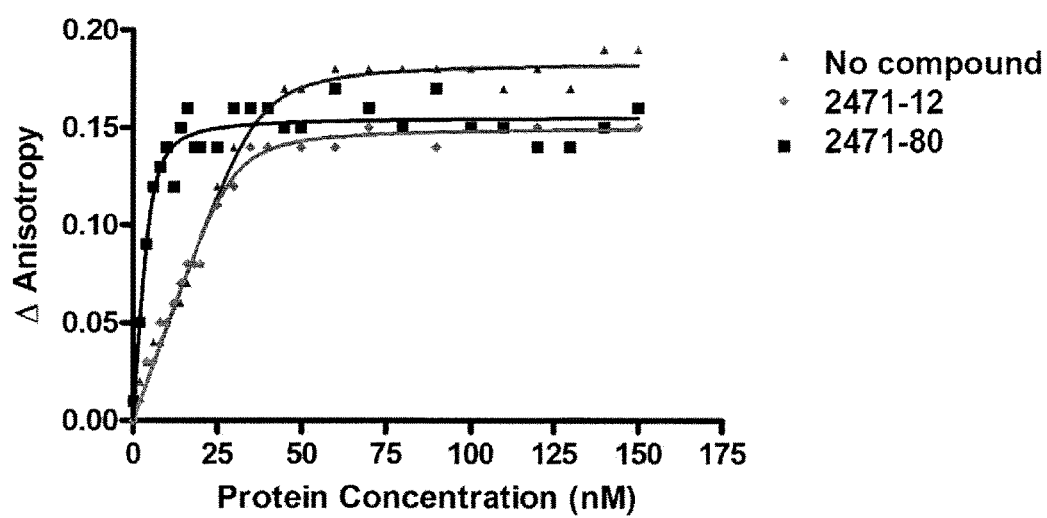
FIG. 6. Effect of 2471-12 and 2471-80 inhibitors on MtTopI DNA binding. Change in anisotropy upon binding of 6-carboxyfluorescein-labeled oligonucleotide (30 nM) to increasing concentration of MtTopI protein was monitored alone, or in the presence of 2471-12 (7.5 μM), 2471-80 (5 μM). Curve fitting was carried out for 1:1 oligonucleotide: MtTopI protein ratio using GraphPad.

Inhibition of MtbTopI Activity at Step Following Formation of Enzyme-DNA Complex Binding of MtbTopI to single-stranded DNA was monitored by the change in anisotropy of an oligonucleotide substrate modified with a fluorescence reporter at the 3'-end. Addition of 2471-12 and 2471-80 at their $IC_{50}$ concentrations did not inhibit the binding of MtbTopI to this oligonucleotide substrate (FIG. 6). The Kd derived from the anisotropy data was found to be decreased from 1.2 nM in the absence of inhibitor to 0.78 nM in the presence of 2471-80 at its $IC_{50}$ concentration. These polyamine-based inhibitors likely interact with the enzyme-DNA complex to inhibit the overall relaxation activity at a step following the initial binding of enzyme to DNA.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "consisting essentially of," as used herein, limits the scope of the ingredients and steps to the specified materials or steps and those that do not materially affect the basic and novel characteristic(s) of the present invention, i.e., compositions and methods for decellularization of tissue grafts. For instance, by using "consisting essentially of," the compositions do not contain any unspecified ingredients including, but not limited to, surfactants that have a direct beneficial or adverse effect on decellularization of tissue.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Friedman N D, Temkin E, Carmeli Y. 2015. The Negative Impact of Antibiotic Resistance. Clin. Microbiol. Infect. doi: S1198-743X(15)01028-9 [pii].
2. Engstrom A. 2016. Fighting an old disease with modern tools: characteristics and molecular detection methods of drug-resistant *Mycobacterium tuberculosis*. Infect. Dis. (Lond). 48:1-17. doi: 10.3109/23744235.2015.1061205 [doi].
3. Matteelli A, Roggi A, Carvalho A C. 2014. Extensively drug-resistant *tuberculosis*: epidemiology and management. Clin. Epidemiol. 6:111-118. doi: 10.2147/CLEP.S35839 [doi].
4. Chen S H, Chan N L, Hsieh T S. 2013. New mechanistic and functional insights into DNA topoisomerases. Annu. Rev. Biochem. 82:139-170. doi: 10.1146/annurev-biochem-061809-100002; 10.1146/annurev-biochem-061809-100002.
5. Vos S M, Tretter E M, Schmidt B H, Berger J M. 2011. All tangled up: how cells direct, manage and exploit topoisomerase function. Nat. Rev. Mol. Cell Biol. 12:827-841. doi: 10.1038/nrm3228; 10.1038/nrm3228.
6. Schoeffler A J, Berger J M. 2008. DNA topoisomerases: harnessing and constraining energy to govern chromosome topology. Q. Rev. Biophys. 41:41-101. doi: 10.1017/S003358350800468X.
7. Aldred K J, Kerns R J, Osheroff N. 2014. Mechanism of Quinolone Action and Resistance. Biochemistry. doi: 10.1021/bi5000564.
8. Tomasic T, Masic L P. 2014. Prospects for developing new antibacterials targeting bacterial type IIA topoisomerases. Curr. Top. Med. Chem. 14:130-151. doi: CTMC-EPUB-57427 [pii].
9. Tse-Dinh Y C. 2009. Bacterial topoisomerase I as a target for discovery of antibacterial compounds. Nucleic Acids Res. 37:731-737. doi: 10.1093/nar/gkn936.

10. Drlica K. 1992. Control of bacterial DNA supercoiling. Mol. Microbiol. 6:425-433.
11. Masse E, Drolet M. 1999. Relaxation of transcription-induced negative supercoiling is an essential function of *Escherichia coli* DNA topoisomerase I. J. Biol. Chem. 274:16654-16658.
12. Tse-Dinh Y C. 2015. Targeting bacterial topoisomerase I to meet the challenge of finding new antibiotics. Future Med. Chem. 7:459-471. doi: 10.4155/fmc.14.157 [doi].
13. Zhang Z, Cheng B, Tse-Dinh Y C. 2011. Crystal structure of a covalent intermediate in DNA cleavage and rejoining by *Escherichia coli* DNA topoisomerase I. Proc. Natl. Acad. Sci. U.S.A. 108:6939-6944. doi: 10.1073/pnas.1100300108.
14. Tan K, Zhou Q, Cheng B, Zhang Z, Joachimiak A, Tse-Dinh Y C. 2015. Structural basis for suppression of hypernegative DNA supercoiling by *E. coli* topoisomerase I. Nucleic Acids Res. 43:11031-11046. doi: 10.1093/nar/gkv1073 [doi].
15. Yamaguchi Y, Inouye M. 2015. An endogenous protein inhibitor, YjhX (TopAI), for topoisomerase I from *Escherichia coli*. Nucleic Acids Res. 43:10387-10396. doi: 10.1093/nar/gkv1197 [doi].
16. Yigit H, Reznikoff W S. 1998. *Escherichia coli* DNA topoisomerase I and suppression of killing by Tn5 transposase overproduction: topoisomerase I modulates Tn5 transposition. J. Bacteriol. 180:5866-5874.
17. Yigit H, Reznikoff W S. 1999. *Escherichia coli* DNA topoisomerase I copurifies with Tn5 transposase, and Tn5 transposase inhibits topoisomerase I. J. Bacteriol. 181: 3185-3192.
18. Pruss G J, Manes S H, Drlica K. 1982. *Escherichia coli* DNA topoisomerase I mutants: increased supercoiling is corrected by mutations near gyrase genes. Cell. 31:35-42. doi: 0092-8674(82)90402-0 [pii].
19. DiNardo S, Voelkel K A, Sternglanz R, Reynolds A E, Wright A. 1982. *Escherichia coli* DNA topoisomerase I mutants have compensatory mutations in DNA gyrase genes. Cell. 31:43-51. doi: 0092-8674(82)90403-2 [pii].
20. Garcia M T, Blazquez M A, Ferrandiz M J, Sanz M J, Silva-Martin N, Hermoso J A, de la Campa A G. 2010. New alkaloid antibiotics that target the DNA topoisomerase I of *Streptococcus Pneumoniae*. J. Biol. Chem. doi: 10.1074/jbc.M110.148148.
21. Suerbaum S, Brauer-Steppkes T, Labigne A, Cameron B, Drlica K. 1998. Topoisomerase I of *Helicobacter pylori*: juxtaposition with a flagellin gene (flaB) and functional requirement of a fourth zinc finger motif. Gene. 210:151-161.
22. Ahmed W, Menon S, Godbole A A, Karthik P V, Nagaraja V. 2014. Conditional silencing of topoisomerase I gene of *Mycobacterium tuberculosis* validates its essentiality for cell survival. FEMS Microbiol. Lett. 353:116-123. doi: 10.1111/1574-6968.12412 [doi].
23. Ravishankar S, Ambady A, Awasthy D, Mudugal N V, Menasinakai S, Jatheendranath S, Guptha S, Sharma S, Balakrishnan G, Nandishaiah R, Ramachandran V, Eyermann C J, Reck F, Rudrapatna S, Sambandamurthy V K, Sharma U K. 2015. Genetic and chemical validation identifies *Mycobacterium tuberculosis* topoisomerase I as an attractive anti-tubercular target. *Tuberculosis* (Edinb). doi: S1472-9792(15)20742-1 [pii].
24. Godbole A A, Ahmed W, Bhat R S, Bradley E K, Ekins S, Nagaraja V. 2014. Inhibition of *Mycobacterium tuberculosis* topoisomerase I by m-AMSA, a eukaryotic type II topoisomerase poison. Biochem. Biophys. Res. Commun. 446:916-920. doi: 10.1016/j.bbrc.2014.03.029 [doi].
25. Tang S C, Shapiro T A. 2010. Newly identified antibacterial compounds are topoisomerase poisons in African trypanosomes. Antimicrob. Agents Chemother. 54:620-626. doi: 10.1128/AAC.01025-09.
26. Cheng B, Liu I, Tse-Dinh Y C. 2007. Compounds with antibacterial activity that enhance DNA cleavage by bacterial DNA topoisomerase I. J. Antimicrob. Chemother. 59:640-645.
27. Bansal S, Sinha D, Singh M, Cheng B, Tse-Dinh Y C, Tandon V. 2012. 3,4-dimethoxyphenyl bis-benzimidazole, a novel DNA topoisomerase inhibitor that preferentially targets *Escherichia coli* topoisomerase I. J. Antimicrob. Chemother. 67:2882-2891. doi: 10.1093/jac/dks322 [doi].
28. Nimesh H, Sur S, Sinha D, Yadav P, Anand P, Bajaj P, Virdi J S, Tandon V. 2014. Synthesis and biological evaluation of novel bisbenzimidazoles as *Escherichia coli* topoisomerase IA inhibitors and potential antibacterial agents. J. Med. Chem. 57:5238-5257. doi: 10.1021/jm5003028 [doi].
29. Houghten R A, Pinilla C, Giulianotti M A, Appel J R, Dooley C T, Nefzi A, Ostresh J M, Yu Y, Maggiora G M, Medina-Franco J L, Brunner D, Schneider J. 2008. Strategies for the use of mixture-based synthetic combinatorial libraries: scaffold ranking, direct testing in vivo, and enhanced deconvolution by computational methods. J. Comb. Chem. 10:3-19. doi: 10.1021/cc7001205.
30. Santos R G, Appel J R, Giulianotti M A, Edwards B S, Sklar L A, Houghten R A, Pinilla C. 2013. The mathematics of a successful deconvolution: a quantitative assessment of mixture-based combinatorial libraries screened against two formylpeptide receptors. Molecules. 18:6408-6424. doi: 10.3390/molecules18066408; 10.3390/molecules18066408.
31. Reilley K J, Giulianotti M, Dooley C T, Nefzi A, McLaughlin J P, Houghten R A. 2010. Identification of two novel, potent, low-liability antinociceptive compounds from the direct in vivo screening of a large mixture-based combinatorial library. AAPS J. 12:318-329. doi: 10.1208/s12248-010-9191-3; 10.1208/s12248-010-9191-3.
32. Wu J, Zhang Y, Maida L E, Santos R G, Welmaker G S, LaVoi T M, Nefzi A, Yu Y, Houghten R A, Toll L, Giulianotti M A. 2013. Scaffold ranking and positional scanning utilized in the discovery of nAChR-selective compounds suitable for optimization studies. J. Med. Chem. 56:10103-10117. doi: 10.1021/jm401543h.
33. Houghten R A, Pinilla C, Appel J R, Blondelle S E, Dooley C T, Eichler J, Nefzi A, Ostresh J M. 1999. Mixture-based synthetic combinatorial libraries. J. Med. Chem. 42:3743-3778.
34. Pinilla C, Appel J R, Blanc P, Houghten R A. 1992. Rapid identification of high affinity peptide ligands using positional scanning synthetic peptide combinatorial libraries. BioTechniques. 13:901-905.
35. Acharya A N, Ostresh J M, Houghten R A. 2002. Determination of isokinetic ratios necessary for equimolar incorporation of carboxylic acids in the solid-phase synthesis of mixture-based combinatorial libraries. Biopolymers. 65:32-39. doi: 10.1002/bip.10206.
36. Ostresh J M, Winkle J H, Hamashin V T, Houghten R A. 1994. Peptide libraries: determination of relative reaction rates of protected amino acids in competitive couplings. Biopolymers. 34:1681-1689. doi: 10.1002/bip.360341212.
37. Nefzi A, Giulianotti M A, Houghten R A. Solid-phase synthesis of bis-heterocyclic compounds from resin-bound orthogonally protected lysine. J Comb Chem, 2001, 3, 68-70. doi: 10.1021/cc000061t.
38. Nefzi A, Ostresh J M, Yu Y, Houghten R A. Combinatorial chemistry: libraries from libraries, the art of the diversity-oriented transformation of resin-bound peptides and chiral polyamides to low molecular weight acyclic and heterocyclic compounds. The Journal of organic chemistry, 2004, 69, 3603-9. doi: 10.1021/jo040114j.
39. Houghten R A. General method for the rapid solid-phase synthesis of large numbers of peptides: specificity of antigen-antibody interaction at the level of individual amino acids. Proc Natl Acad Sci USA, 1985, 82, 5131-5. doi: 10.1073/pnas.82.15.5131.
40. Ostresh J M, Schoner C C, Hamashin V T, Nefzi A, Meyer J P, Houghten R A. Solid-Phase Synthesis of Trisubstituted Bicyclic Guanidines via Cyclization of Reduced N-Acylated Dipeptides. The Journal of Organic Chemistry, 1998, 63, 8622-8623. doi: 10.1007/BF02854908.
41. Nefzi A, Ostresh J M, Houghten R A. Parallel solid phase synthesis of tetrasubstituted diethylenetriamines via selective amide alkylation and exhaustive reduction of N-acylated dipeptides. Tetrahedron, 1999, 55, 335-344. doi: 10.1016/S0040-4020(98)01043-6.
42. Manku S, Laplante C, Kopac D, Chan T, Hall D G. A mild and general solid-phase method for the synthesis of chiral polyamines. Solution studies on the cleavage of borane-amine intermediates from the reduction of secondary amides. The Journal of organic chemistry, 2001, 66, 874-85. doi: 10.1021/jo005647g.
43. Williams K J, Joyce G, Robertson B D. 2010. Improved mycobacterial tetracycline inducible vectors. Plasmid. 64:69-73. doi: 10.1016/j.plasmid.2010.04.003.
44. Andreu N, Zelmer A, Fletcher T, Elkington P T, Ward T H, Ripoll J, Parish T, Bancroft G J, Schaible U, Robertson B D, Wiles S. 2010. Optimisation of bioluminescent reporters for use with mycobacteria. PLoS One. 5:e10777. doi: 10.1371/journal.pone.0010777; 10.1371/journal.pone.0010777.
45. Narula G, Tse-Dinh Y C. 2012. Residues of *E. coli* topoisomerase I conserved for interaction with a specific cytosine base to facilitate DNA cleavage. Nucleic Acids Res. 40:9233-9243. doi: 10.1093/nar/gks688; 10.1093/nar/gks688.

We claim:
1. A compound comprising a polyamine scaffold, wherein the compound has the following general structure:

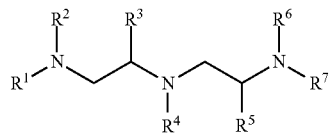

wherein $R^1$, $R^2$, $R^3$, $R^4$, and $R^6$ are, independently, hydrogen, alkyl, substituted alkyl, aryl, substituted aryl, heteroaryl, substituted heteroaryl, cycloalkyl, substituted cycloalkyl, cycloalkenyl, substituted cycloalkenyl, alkenyl, alkynyl, acyl, haloalkyl, thiol, amino, alkylamino, hydroxyl, hydroxylalkyl, or —COOH; $R^5$ is alkyl, amino, or substituted alkyl, the substituted group being selected from amino, naphthyl, alkylamino and guanidine; and $R^7$ is a substituted alkyl, the substituted group being naphthyl.

2. The compound according to claim 1, wherein $R^1$, $R^2$, $R^4$, and $R^6$, are hydrogen; and $R^3$ is hydrogen, alkyl, amino, or substituted alkyl, the substituted group being selected from amino, naphthyl, and alkylamino.

3. The compound according to claim 1, wherein $R^7$ is a substituted methyl or ethyl, the substituted group being naphthyl.

4. The compound according to claim 1, wherein $R^3$ and $R^5$ are, independently, alkyl, amino, or substituted alkyl, the substituted group being selected from amino, naphthyl, and alkylamino.

5. The compound according to claim 1, wherein at least one of $R^3$ and $R^5$ is a substituted alkyl, the substituted group being naphthyl.

6. The compound according to claim 5, wherein at least one of $R^3$ and $R^5$ is a substituted methyl or ethyl, the substituted group being naphthyl.

7. The compound according to claim 1, wherein at least one of $R^3$ and $R^5$ is a substituted alkyl, the substituted group being amino.

8. The compound according to claim 1, wherein at least one of $R^3$ and $R^5$ is a substituted alkyl, the substituted group being alkylamino.

9. The compound according to claim 1, wherein $R^5$ is a substituted alkyl, the substituted group being guanidine.

10. The compound according to claim 1, which is compound 2471-12, 2471-24, 2471-36, 2471-80, 2580-3, 2580-15, 2580-18, 2580-24, 2580-27, or 2580-33.

11. A pharmaceutical composition for treating a bacterial infection comprising a compound of claim 1 and a pharmaceutically acceptable carrier.

* * * * *